(12) United States Patent
Soden et al.

(10) Patent No.: US 11,912,975 B2
(45) Date of Patent: Feb. 27, 2024

(54) ELECTROPORATION APPARATUS AND METHOD

(71) Applicant: MIRAI MEDICAL LIMITED, Oranmore (IE)

(72) Inventors: Declan Soden, Clonakilty (IE); Colin Forde, Kinvara (IE); Sean Kinsella, Oranmore (IE); Tony Moore, Ballincollig (IE)

(73) Assignee: MIRAI MEDICAL LIMITED, Oranmore (IE)

( * ) Notice: Subject to any disclaimer, the term of this patent is extended or adjusted under 35 U.S.C. 154(b) by 0 days.

(21) Appl. No.: 17/636,649

(22) PCT Filed: Sep. 1, 2020

(86) PCT No.: PCT/EP2020/074374
§ 371 (c)(1),
(2) Date: Feb. 18, 2022

(87) PCT Pub. No.: WO2021/043779
PCT Pub. Date: Mar. 11, 2021

(65) Prior Publication Data
US 2022/0298464 A1    Sep. 22, 2022

(30) Foreign Application Priority Data

Sep. 2, 2019  (EP) ..................................... 19194958
Sep. 2, 2019  (EP) ..................................... 19194959
Apr. 7, 2020  (EP) ..................................... 20168567

(51) Int. Cl.
*C12M 1/42*       (2006.01)
*A61N 1/32*        (2006.01)
*A61B 18/00*      (2006.01)

(52) U.S. Cl.
CPC ............. *C12M 35/02* (2013.01); *A61N 1/327* (2013.01); *A61B 2018/00613* (2013.01); *A61B 2018/00875* (2013.01)

(58) Field of Classification Search
CPC ...... C12M 35/02; C12M 35/04; C12M 25/02; C12M 23/12; A61N 1/327; A61N 1/306;
(Continued)

(56) References Cited

U.S. PATENT DOCUMENTS 5,702,359 A      12/1997  Hofmann et al.
5,869,326 A *    2/1999   Hofmann ............... C12N 15/87
                                                                  435/283.1
(Continued)

FOREIGN PATENT DOCUMENTS

WO    2005/048977 A2    6/2005
WO    2018/200800 A1    11/2018

OTHER PUBLICATIONS

International Search Report issued in PCT/EP2020/074374; dated Feb. 4, 2021.
(Continued)

*Primary Examiner* — Michael L Hobbs
(74) *Attorney, Agent, or Firm* — Studebaker & Brackett PC

(57) ABSTRACT

An electroporation apparatus has an electroporation probe terminals for linking with electrodes. A foam is injected at the treatment site to displace blood rather than mixing with it, increasing the contact time of a higher concentration of active agent with the tissue and thus resulting in greater efficacy. With foam solutions, a lower concentration of agent can be used to obtain the same therapeutic effect as in their liquid counterpart, reducing the prevalence of side effects associated with higher concentrations. A foam solution compared to an equivalent liquid solution enables more
(Continued)

efficient cell electroporation particularly where bipolar pulses have been employed by mitigating an increase in tissue conductivity as would normally be observed with a comparable liquid solution. A more efficient cell permeabilization would result in better results where electroporation is being delivered alone or as a tool to aid in the uptake of molecules into the cell.

22 Claims, 11 Drawing Sheets

(58) Field of Classification Search
CPC ...... A61B 18/1477; A61B 2018/00113; A61B 2018/0016; A61B 2018/00767; A61B 2018/00875; A61B 2018/143; A61B 2018/1206; A61B 2018/00613; A61B 2018/124; C12N 13/00; C12N 15/87; C12N 15/8207; C12N 15/8206; A61K 48/00; A61K 38/00; H03K 3/57
See application file for complete search history.

(56) References Cited

U.S. PATENT DOCUMENTS

| | | |
|---|---|---|
| 6,096,020 A | 8/2000 | Hofmann |
| 2006/0089674 A1 | 4/2006 | Walters et al. |
| 2008/0312579 A1 | 12/2008 | Chang et al. |
| 2014/0188071 A1 | 7/2014 | Jacofsky et al. |
| 2017/0246468 A1* | 8/2017 | Kalghatgi ................ A61N 1/44 |
| 2017/0348525 A1 | 12/2017 | Sano et al. |

OTHER PUBLICATIONS

Ibey et al., Bipolar nanosecond electric pulses are less efficient at elecropermeabilization and killing cells than monopolar pulses., Biochem. Biophys. Res. Commun., Jan. 10, 2014, pp. 568-573, vol. 443, No. 2.

Polajžer et al., Cancellation effect is present in high-frequency reversible and irreversible electroporation, Bioelectrochemistry, Apr. 2020, 132:107442, Elsevier, Epub Dec. 24, 2019, PubMed, https://doi.org/10.1016/j.bioelechem.2019.107442.

* cited by examiner

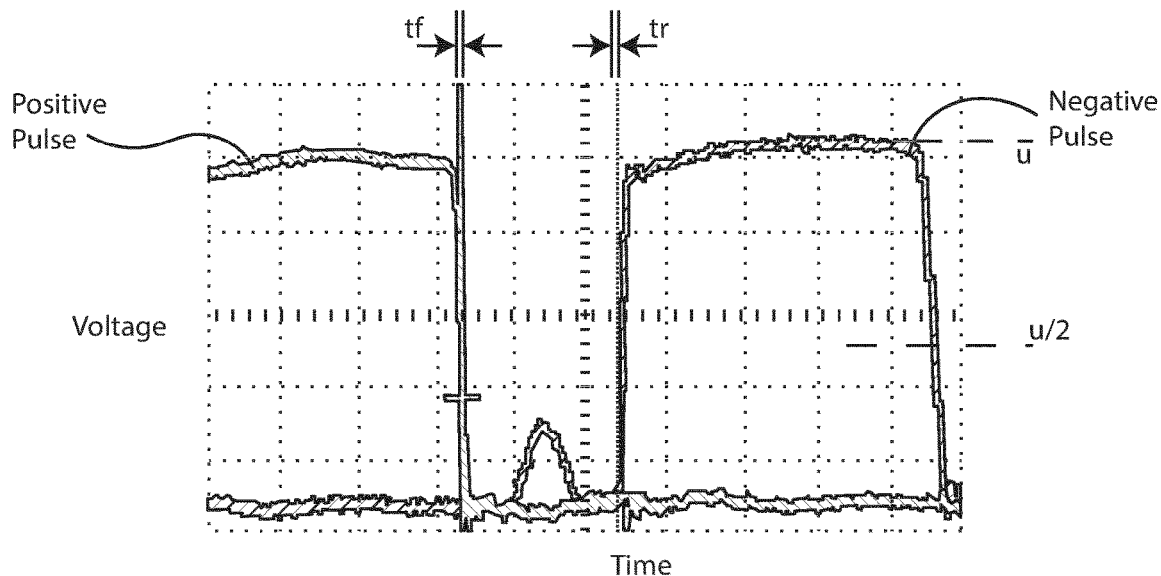
Fig.10
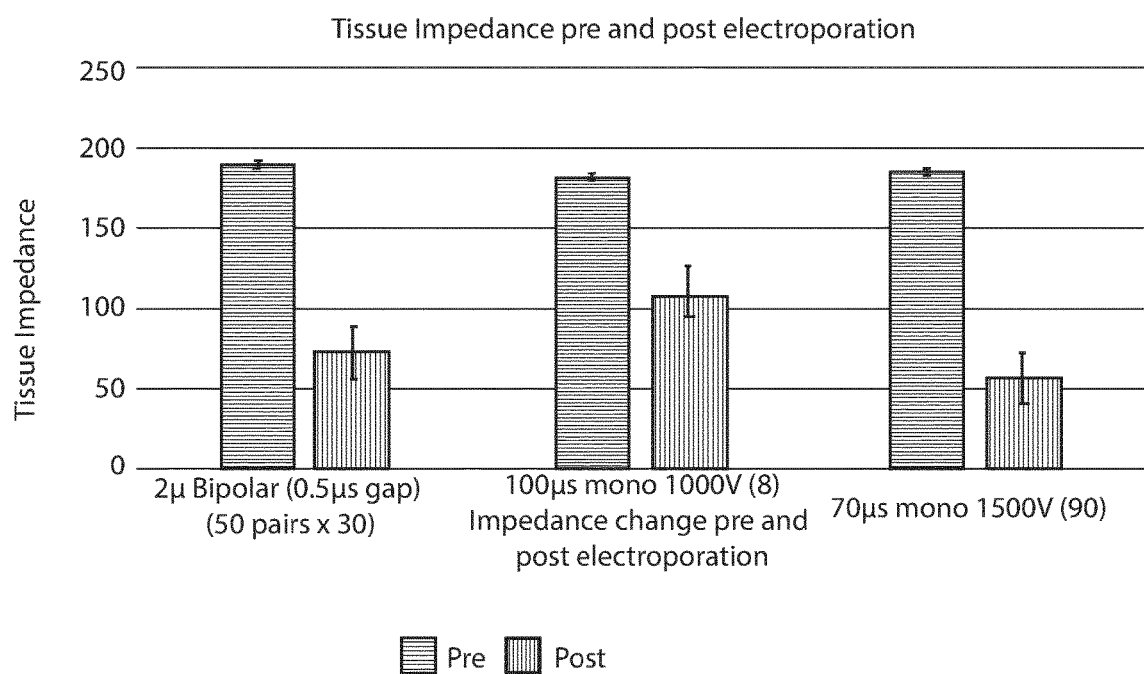
Fig.11, Effect of High frequency v standard low frequency electroporation pulses on Potato tissue

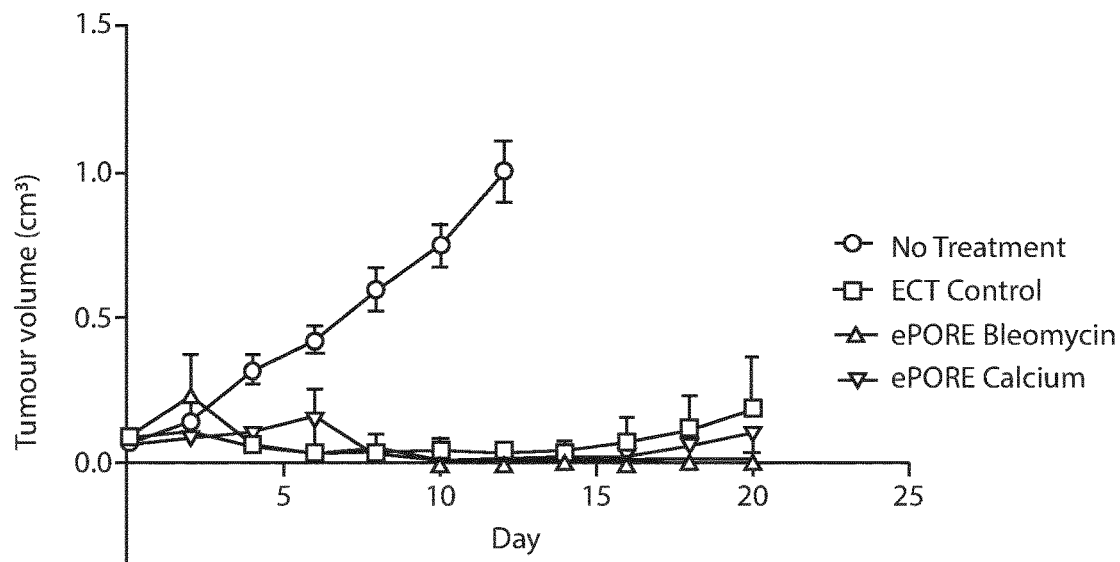
Fig.12, Effect of High frequency electroporation v standard low frequency in a murine tumour model when combined with drugs.
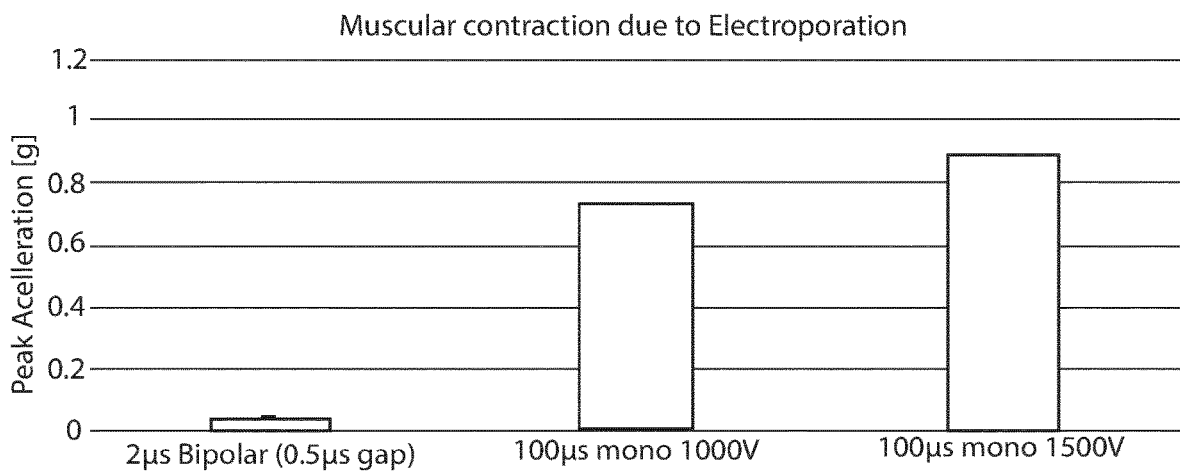
Fig.13, Reduced muscular contractions due to High frequency electroporation

ELECTROPORATION APPARATUS AND METHOD

INTRODUCTION

The invention relates to electroporation.

US2006/089674 (Walters et al) and WO2018/200800 (bowers et al) describe electroporation apparatus'.

Electroporation is a medical and molecular biology technique in which an electric field is applied to cells in order to increase the permeability of the cell membrane, allowing molecules previously impervious to the cell to be introduced. Electroporation has a number of possible fields of application, and can be used where its effects on the cell membrane are reversibly and irreversibly applied. In a typical electroporation process, short and intense electric pulses are generated to transiently permeabilize the cell membrane.

In reversible electroporation, which may be used in relation to enable for example the intracellular passive diffusion of chemotherapy, the electric field is below a certain voltage threshold and allows the cell membrane to repair after the treatment. Reversible electroporation may involve allowing a molecule, such as a drug or gene, into a cell or molecule that is normally not permeable for this substance without inducing cell death from the electrical field alone. The electric field threshold for a cell is individual for the cell. In irreversible electroporation the electric field is greater than this voltage threshold, which creates permanent nanopores in the cell membrane, disrupting the cellular homeostasis and consequently the cell dies by a combination of apoptosis and necrosis due to a disruption of normal cellular function.

The invention is directed towards providing an electroporation probe drive and apparatus and method for delivering high-voltage, ultra-short electroporation pulses (microsecond range preferably, and in some cases down to the nanosecond range) at close to the theoretical ideal, with sharp turn-on and turn-off times, and a stable amplitude when applied to a biological load.

A further object is to avoid requirement for a physically large size of the drive apparatus.

A further object is directed towards achieving a more favourable treatment environment surrounding the cells being treated.

REFERENCES

Reference: B. L. They et al., Bipolar nanosecond electric pulses are less efficient at elecropermeabilization and killing cells than monopolar pulses, Biochem. Biophys. Res. Commun., vol. 443, no. 2, pp. 568☐73, January 2014. 10.1016/j.bbrc.2013.12.004.

Reference: Polajžer T, Dermol-Černe J, Reberšek M, O'Connor R, Miklavčič D. Cancellation effect is present in high-frequency reversible and irreversible electroporation. Bioelectrochemistry. 2020 April; 132:107442. doi: 10.1016/j.bioelechem. 2019.107442. Epub 2019 Dec. 24. PubMed PMID:31923714.

SUMMARY

Typically, electroporation treatments incorporate pulse lengths in the 50-100 µsec range with pulses used alone (irreversible electroporation) or in combination with chemotherapy (electrochemotherapy) to induce cell death. More recently shorter microsecond (<10 µsec) high frequency irreversible electroporation and nanosecond (<1 µsec) pulses have been explored with a cancellation effect on the degree of cell permeabilization being observed when using bipolar compared to monopolar pulses.

In the invention we provide apparatus and methods to achieve an improved environment around the cells being treated. These improvements arise from our understanding that in the short microsecond range (<10 µsec) there may be a cancellation effect (reduced cell permeabilization) when using bipolar pulses and which is in part determined by the conductivity of the solution surrounding the cells. The efficacy of cell permeabilization (pores being created on the cell membrane) created by short bipolar electrical pulses (<10 µs) is impacted by the conductivity where a lower conductivity would enable a more efficient electrical pulse induced cell membrane permeabilization. The conductivity around the cell is influenced in part by the volume of fluid in the area and the local injection of a solution such as a local anaesthetic or other ion-containing solution. An increase in conductivity surrounding the cells to be electroporated will result in higher currents which is deleterious to the treatment resulting in poorer cell permeabilization and pain sensation in the patient. In a highly conductive environment, the electroporation treatment may give rise to gases during the treatment causing a pressure wave (referred to as discharges, sparks or arcing) with severe acoustic manifestation and mechanical tissue damage. The cell lysis and release of ions that occurs during the electroporation process in itself will cause an increase in tissue conductivity, resulting in high currents and potential machine failure and inadequate pulse delivery.

In the following we describe an improved electroporation apparatus to provide pulses, substances for use in improving the environment around cells being treated, and an improved probe head for both injection of a substance and for applying the electroporation pulses in any desired order with the same needles inserted into the tissue.

We describe an electroporation apparatus comprising a plurality of electroporation probe terminals, a transformer for providing stepped-up voltage, and a switching circuit for delivering pulses to the probe terminals for electroporation. The switching circuit preferably has switches for linking high voltage and low voltage or ground levels to the probe terminals, and a controller configured to control said switches according to a control scheme to deliver pulses to the probe terminals, and in which said pulses are delivered to groups of at least two probe electrode terminals for probe electrodes which are spaced apart.

Preferably, the pulses are bipolar for a pair of electrodes. Preferably, each terminal of a pair is sequentially driven at a voltage amplitude and grounded out of phase with its corresponding probe terminal.

Preferably, the controller is configured to apply a ramp-up ($t_r$) duration of less than 0.5 µs to a plateau (U) amplitude in the range of 100V to 3000V for a duration in the range of 1 µs to 5 µs, and a ramp-down ($t_f$) duration from said voltage of less than 0.5 µs for each probe electrode terminal.

Optionally, the amplitude is in the range of 700V to 1600V and the pulse plateau duration is in the range of 1 µs to 3 µs, and preferably the energized on time during which pulses are delivered is in the range of 100 µs to 300 µs. Preferably, pulses are delivered in immediate succession. Preferably, the bipolar frequency is in the range of 100 kHz to 500 kHz.

Preferably, the controller is configured to apply, after electroporation operation, a plateau of near to zero duration and to allow a ramp-down decay in a pulse, and preferably the rate of decay is set by permanent or adjustable values of resistors across charged capacitors.

Optionally, the controller is configured with mapping data defining relative physical positions of probe terminals to be connected to the terminals, and to direct pulses for applying voltages across space bounded by the probe electrodes.

Preferably, the controller is configured to simultaneously drive a first group of terminals with the same potential and an opposed second group with a different potential, for application of a charge across and between a plane defined by said first and second mapped probe locations.

Optionally, the first group are driven with a high potential and the second group are grounded.

Preferably, the controller is configured to immediately reverse the direction across the plane, with the first group being applied with the potential previously applied to the second group and vice versa, in which the first and second groups are re-defined so that charge is applied in one direction across the space and then immediately reversed.

Preferably, the controller is configured to, after reversing the direction across the plane, then drive third and fourth groups which also define said plane but the direction between the third and fourth groups is different from that between the first and second groups.

Preferably, said directions are approximately orthogonal. Preferably, the mapping data is for a plane defined by at least one quadrangle bounded by four probes. Preferably, the mapping data is for a plurality of quadrangles.

Optionally, the mapping data defines the quadrangles with some probes having roles in defining sides of different and adjoining quadrangles.

Preferably, the switching circuit comprises a switch dedicated to each voltage level for each terminal. Preferably, the switching circuit comprises a switch dedicated to a high voltage level applied as a pulse to a terminal, and a switch dedicated to grounding the terminal.

Preferably, the switching circuit comprises a driver circuit dedicated to each switch. Preferably, each driver circuit is individually addressable by the controller. Optionally, each driver circuit comprises an independent floating power supply. Preferably, the switches include FETs and/or IGBTs.

Preferably, the controller is configured to perform a probe interrogation initially, to determine from a probe memory a desired driving profile. Preferably, the probe interrogation is performed by the controller to set the optimal parameters for the probe.

Preferably, the controller is configured to measure the impedance in a biological load by applying an AC signal to probe electrodes over a frequency spectrum. Preferably, the frequency spectrum is in the range of 1 kHz to 100 kHz. Preferably, the impedance measurement is performed before electroporation driving, and the controller is configured to automatically adjust drive parameters according to said measured impedance, preferably to achieve a current flow across a pair of electrodes of less than 500 mA.

We also describe an electroporation apparatus of any example described herein and a plurality of probe electrodes connected to said probe terminals.

In one example, the probe electrodes are in a probe head comprising at least one electrode needle which is hollow and has at least one opening for flow of a substance into tissue before, and/or during, and/or after electroporation. Preferably, the controller is configured to control flow of a substance to the one or more needles in a method also including driving the needles with pulses.

We also describe a method of operation of such an apparatus, the method comprising the steps of inserting said probe electrodes into a biological load and the apparatus applying bi-polar voltage pulses into the electrodes and the load for electroporation.

Preferably, the controller applies the pulses of opposed probe electrodes in a bipolar manner Preferably, the pulse plateau (U) duration ($\Delta t$) is in the range of 1 µs to 5 µs, preferably 1 µs to 3 µs. Preferably, the pulse plateau voltage amplitude (U) is in the range of 100V to 3000V, preferably 700V to 1600V.

Preferably, the energized on-time duration of active treatment, in which the probe electrodes are pulsed, is in the range of 100 µs to 300 µs, and the bipolar pulse frequency based on a cycle of two successive pulses is in the range of 100 kHz to 500 kHz.

Preferably, the electrodes are driven so that current flow in the probe electrodes and the biological load is less than 500 mA for migration of DNA into permeabilized cells.

Preferably, there is irreversible electroporation in which an hyperosmotic solution is injected to the site to assist a process of cell ablation, and said solution may include Calcium.

Preferably, Calcium ions ($Ca^{++}$) are injected intratumourally at a concentration in the range of 2 mMol/L to 250 mMol/L and preferably in the range of 2 mMol/L to 150 mMol/L.

Preferably, a solution comprising calcium ions ($Ca^{++}$) with a concentration of a 2 mMol/L to 150 mMol/L is injected for transient permeabilization by electroporation with an applied pulse voltage of 500 V/cm to 1500 V/cm; a pulse plateau duration of 1 µs to 3 µs, a pulse number in the range of 1000 to 10,000.

In other preferred examples Calcium ions ($Ca^{++}$) are injected intratumourally at a concentration in the range of 2 mMol/L to 250 mMol/L and preferably in the range of 2 mMol/L to 150 mMol/L.

In other preferred examples, a solution comprising calcium ions ($Ca^{++}$) with a concentration of a 2 mMol/L to 150 mMol/L is injected for transient permeabilization by electroporation with an applied pulse voltage of 500 V/cm to 1500 V/cm; a pulse plateau duration of 1 µs to 3 µs, a pulse number in the range of 1000 to 10,000.

In one example, there is delivery of DNA to cells in reversible electroporation in the steps of:
(a) injection of the DNA to the site,
(b) insertion of the probe electrodes,
(c) driving pulses to the electrodes to permeabilize the cells, said driving being bipolar pulses at a frequency in the range of 100 kHz and 500 kHz; a pulse plateau duration in the range of 1 µs to 5 µs and preferably 1 µs to 3 µs; and a voltage amplitude in the range of 100V to 3000V; and
(d) low frequency electrode driving to draw the DNA or agent into the cells in an electrophoretic phase low-voltage pulses of less than 5V for a pulse duration of 10 ms to 100 ms.

In one example, a drug is injected into the site and electroporation takes place for migration of the drug into the cells to cause cell ablation, for example chemotherapy agents.

In one example, the controller, after pulsed driving of the electrodes, discharges stored charge in a pulse of near zero duration followed by exponential decay.

In one example, the controller measures impedance of the biological load between at least one pair of electrodes and automatically sets a pulse voltage amplitude to avoid excessive current flow during electroporation.

We also describe a method of performing electroporation in a subject, the method comprising the steps of injecting a liquid to a target environment surrounding cells to be treated, and electroporation probes delivering pulses to the site.

The liquid is preferably for many examples of use in the form of a foam, having a liquid and bubbles of a gas. Preferably, the foam is delivered to achieve a higher impedance and therefore lower conductivity than a liquid. Preferably, the foam includes a foaming agent to assist mixing of the gas. The gas in the foam may include air and/or CO2. Preferably, ratio of gas to liquid is approximately in a range of 1:2 to 1:10 by volume. Preferably, the foaming agent includes one or more of Albumin and human serum albumin. Preferably, the foaming agent concentration is in the range of 5% to 80% w/w. Preferably, the foaming agent includes Polidocanol or Sodium Tetradecyl Sulfate (STS).

Preferably, the liquid comprises an active agent treatment composition. Preferably, the composition includes one or more selected from Calcium, Potassium, Bleomycin, Cisplatin, DNA, RNA. Preferably, the treatment composition comprises one or more of Calcium ions, Potassium ions, Bleomycin, Cisplatin, DNA or RNA.

The liquid has preferably for some uses a concentration of ions, for example Calcium or Potassium ions at a concentration of 2 mMol to 250 mMol, or more preferably of 2 mMol to 150 mMol Preferably, the electrical pulses have a pulse length in the range of 0.05 µs to 5 µs.

Preferably, for many treatments, the electrical pulses are bipolar.

Preferably, the electrical pulses are delivered in trains with an 'on' energised time per train in the range of 1 µs to 1000 µs repeated up to 1000 times at a frequency in the range of 1 KHz to 1000 KHz.

In some examples, the treatment is electrochemotherapy, the pulse voltage is in the range of 500V/cm to 1500V/cm, and/or the pulse duration is in the range of 50 µsec to 100 µsec, and/or the pulse frequency is in the range of 1 Hz to 5000 Hz, and/or the number of pulses is in the range of 4 to 8.

In some examples, the treatment is irreversible electroporation, the pulse voltage is in the range of 1500V/cm to 3000 V/cm, and/or the pulse duration is in the range of 70 to 100 µsec, and/or the pulse frequency is in the range of 0.5 Hz to 10 Hz to, and/or the number of pulses is in the range of 90 to 200.

In some examples, the treatment is high frequency irreversible electroporation, the pulse voltage is in the range of 2500V/cm to 5000V/cm, and/or the pulse duration is in the range of 1 µsec to 5 µsec, and/or the pulse frequency is in the range of 100 kHz to 500 kHz, and/or the number of pulses is greater than 100.

In some examples, the treatment is electroporation and electrolysis (E2), the pulse voltage is in the range of 100V/cm to 3000V/cm, and/or the charge delivered is greater than 100 µF, and/or the pulse is an exponentially decaying wave.

We also describe a method in which the treatment is DNA or RNA delivery, the pulse voltage is in the range of 1V/cm to1000V/cm, and/or pulse is a monopolar square wave.

In one aspect, the liquid, preferably in the form of a foam, provides dispersion of a local anaesthetic into the tissue to be treated. In one aspect, the local anaesthetic includes lignocaine (also known as "lidocaine"). In one aspect, the local anaesthetic includes lignocaine in a proportion of 5 to 20 mg/ml with or without adrenaline. In one aspect, the local anaesthetic includes mepivacaine. In one aspect, the local anaesthetic includes mepivacaine in a proportion of 10 to 30 mg/ml.

In one aspect, the liquid with an anaesthetic, preferably in the form of a foam, is administrated in combination with a molecule of choice such as any one or more of Calcium ions, Potassium ions, Bleomycin, DNA.

We also describe a foam for use in assisting permeabilization or ablation of cells during electroporation.

Preferably, the foam comprises a treatment composition. Preferably, the composition includes one or more selected from Calcium, Potassium, Bleomycin, Cisplatin, DNA, RNA.

Preferably, the foam has a concentration of ions. Preferably, the foam comprises Calcium ions with a concentration of 2 mMol to 150 mMol.

In one preferred example, the foam comprises an anaesthetic in combination with a molecule of choice such as any one or more of Calcium ions, Potassium ions, Bleomycin, DNA.

We also describe an electroporation probe head comprising at least one electrode needle which is hollow and has at least one opening for flow of a substance into tissue before, and/or during, and/or after electroporation.

Preferably, there are a plurality of needles. The needles may have a maximum internal width dimension in the range of 0.1 mm to 1.8 mm and a maximum external width dimension in the range of 0.25 mm to 2.5 mm, and the openings may have a maximum width dimension in the range of 0.05 mm to 1.5 mm.

In one example there a plurality of needles and the separation of the needles is in the range of 2 mm to 3 cm.

The openings may be arranged in a spiral or staggered manner along length of a needle. The openings may have a greater distribution on a side of at least one needle facing another needle.

We also describe an electroporation apparatus comprising a pulse generator linked with a probe head comprising at least one electrode needle which is hollow and has at least one opening for flow of a substance into tissue before, and/or during, and/or after electroporation.

Preferably, the apparatus comprises a controller adapted to control delivery of pulses to the needles and to control delivery of a substance to the needles according to a desired method.

Preferably, the controller is configured to cause, in order, delivery of a first substance to at least some needles, pulsing of said needles, and delivery of a second substance to said needles. Preferably, the first substance has a lower conductivity than the second substance. In one example, the first substance comprises a foam. In one example, the first substance comprises a foam and the second substance comprises a foam, and the first substance foam has a greater gas concentration than the second substance foam.

We also describe a method of operation of an electroporation apparatus comprising pumping a substance through the needles to flow out via the openings and applying pulses to the needles. The method may include delivering a substance through the needles in advance of application of the pulses and/or after application of the pulses.

DETAILED DESCRIPTION OF THE INVENTION

The invention will be more clearly understood from the following description of some embodiments thereof, given by way of example only with reference to the accompanying drawings in which:

FIG. 10 is an image of a sample pulse captured by a CRO;

FIG. 11 is a set of plots showing tissue impedance before and after electroporation;

FIG. 12 is a set of plots of tumour volume change for four scenarios for comparison purposes;

FIG. 13 is a plot of muscular contractions due to electroporation, showing benefits for smaller time durations and higher frequencies;

Figure 1:
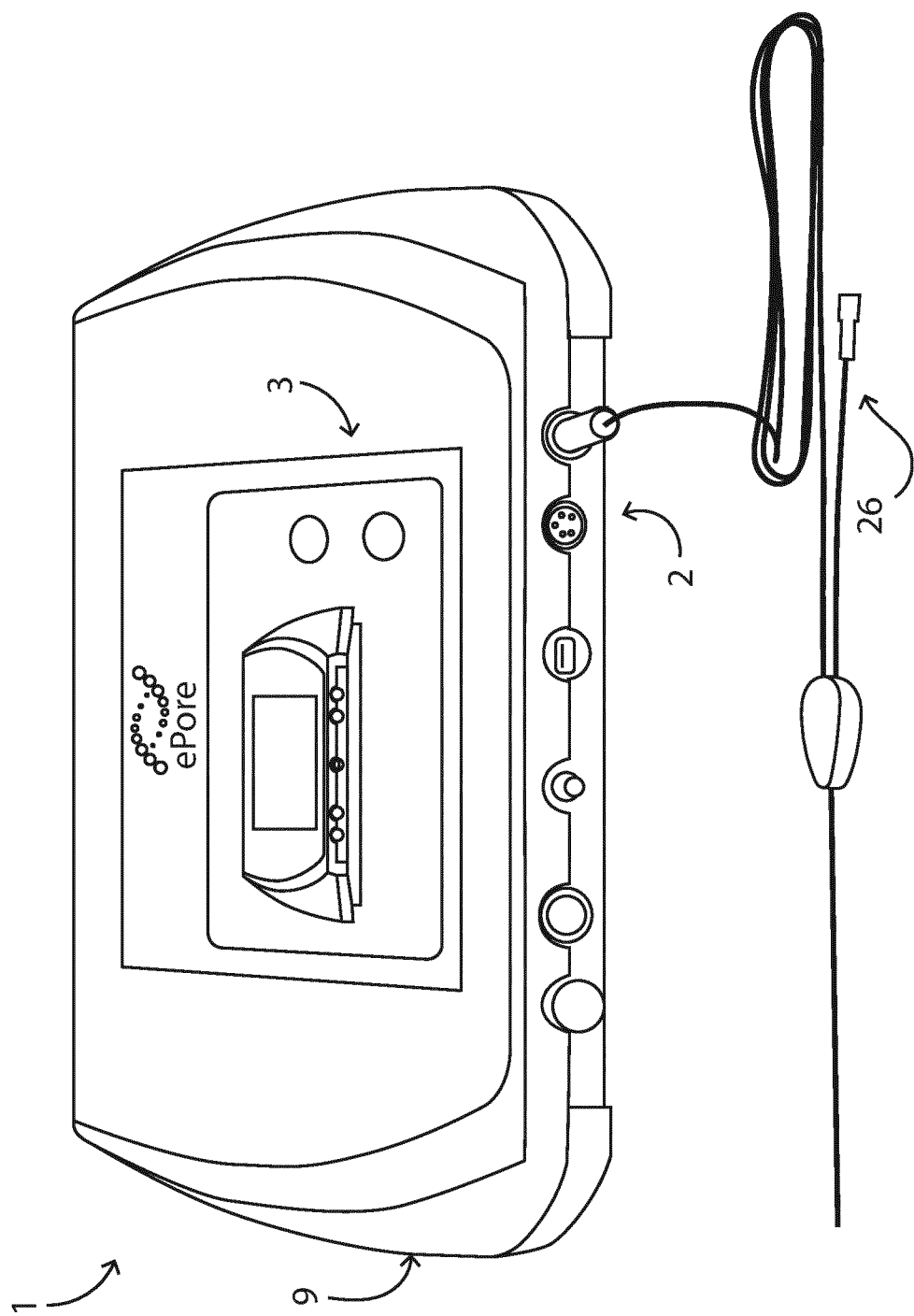
FIG. 1 is a perspective view of an electroporation apparatus.
Figure 2:
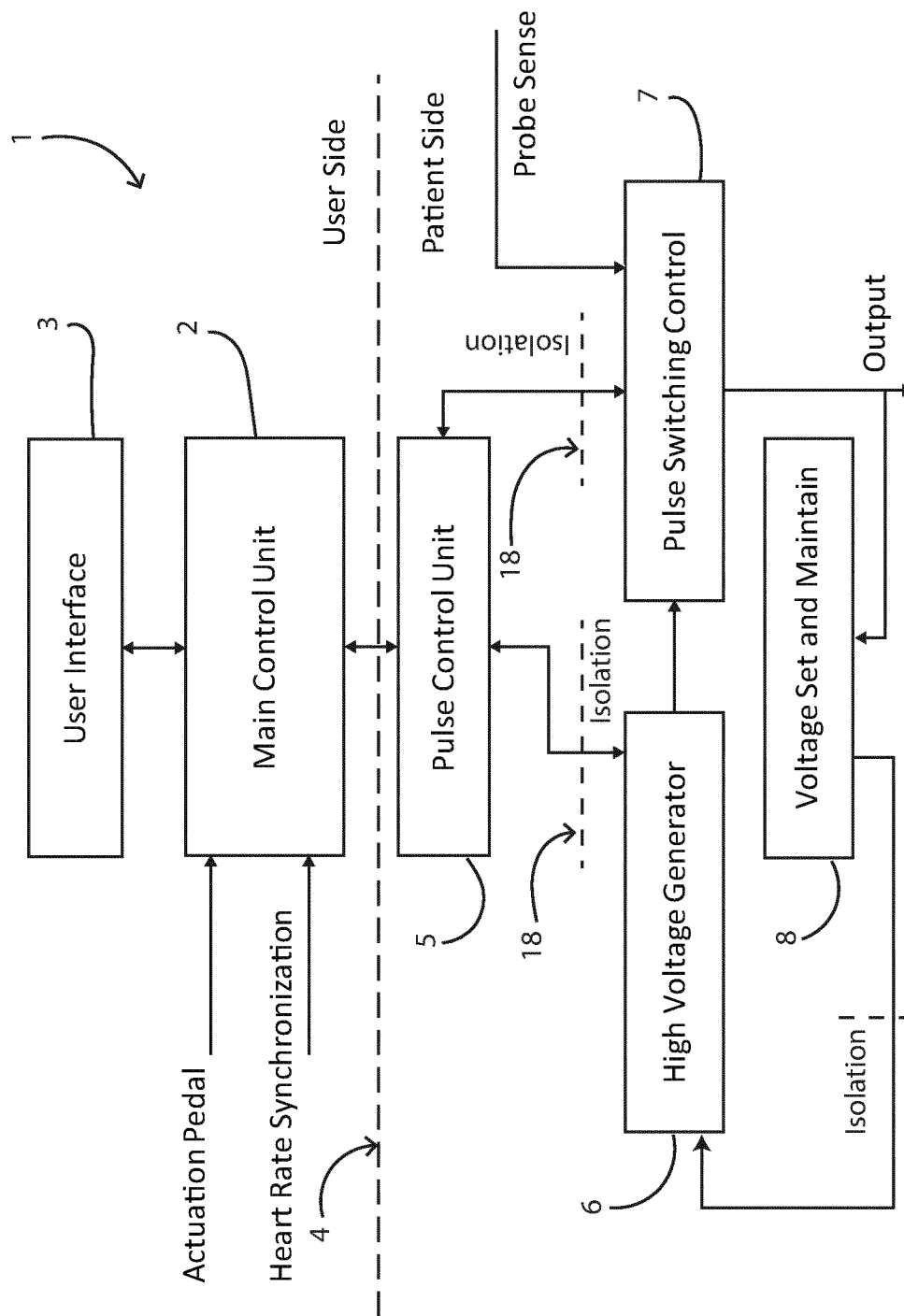
FIG. 2 is a block diagram of the apparatus.

Referring to FIGS. 1 and 2, an electroporation apparatus 1 comprises a main controller 2 linked with a user interface 3 and with a probe drive circuit 4, all mounted in a housing 9. The controller 2 and the interface 3 provide the user-side functions, whereas the drive circuit 4 provides the pulses to a probe 26.

The drive circuit 4 comprises:
a pulse control unit 5 which is separated by opto-isolators 18 from the remainder of the drive apparatus 4, to avoid high voltages being inadvertently transferred to the low-voltage control electronics,
a high voltage generator 6 with a transformer, providing up to 1.5 kV across capacitors, as described in more detail below with reference to FIG. 3,
a pulse switching controller 7, as described in more detail with reference to FIG. 4, for delivering high frequency bi-polar pulses to an array of seven probe electrodes 26, and a voltage set and maintain circuit 8.

The touch screen interface 3 is operably coupled to the controller 2 which manages the generation of the high voltages and the pulse control, and the voltage, pulse duration, polarity and orientation. This level of control is achieved via the series of control circuits in the blocks 5-8.

Figure 3:
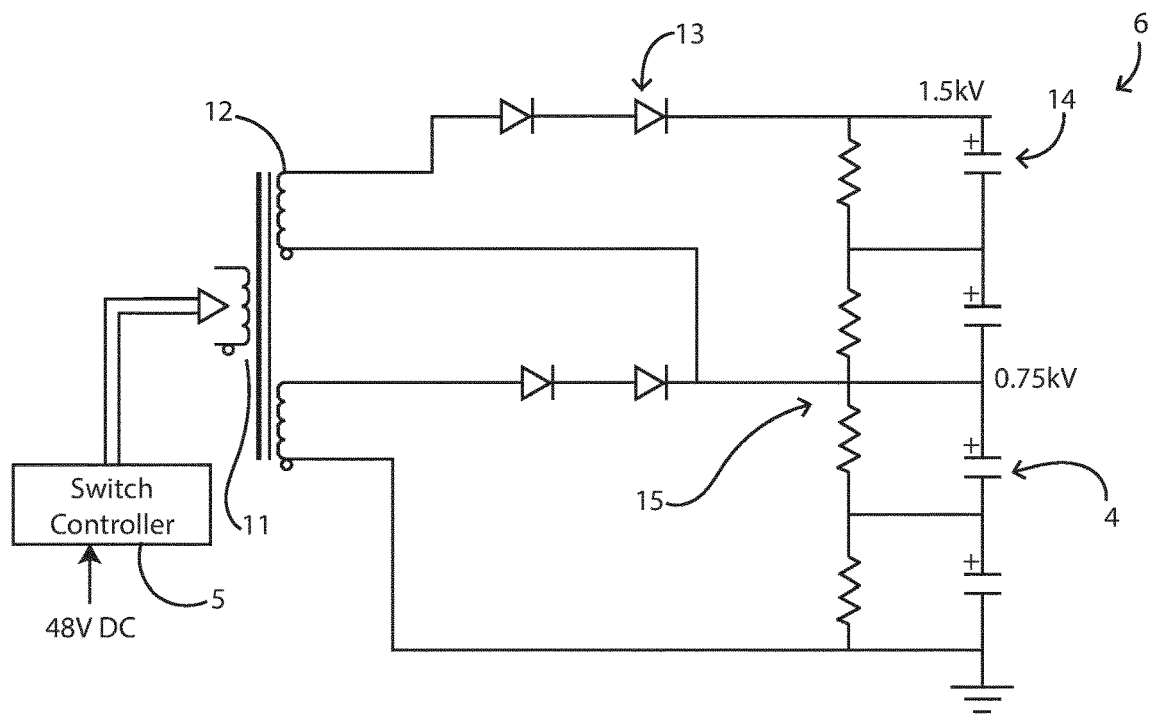
FIG. 3 shows a high voltage generator with a transformer.

The high voltage generator 6 is shown in FIG. 3. The switch controller 5 which receives a low-voltage DC input of say 48 V. This input level sets the resultant pulse intensity level delivered to the probe 26, as described below. The switch controller 5 adjusts the time that the transformer primary 1 is energised to control the output voltage on the capacitors 14. Feedback from the output to the switch controller 5 (with suitable isolation through the medical grade optocoupler devices 18) enables the voltage to be precisely set and maintained. Thus, the capacitor 14 output voltage can be varied over a large range (typically 100V to about 1.5 KV).

The transformer 11, 12 steps up the input voltage to 1.5 kV in this example, which is rectified by a rectifier 13 of conventional construction. This high voltage level, now DC, appears across balance resistors 15 and 1000 µF capacitors 14 as an output to the probe electrodes (26). Each of the four capacitors 14 handles up to 450 V each in this example. The charge time is less than 10 seconds.

The diodes 13 withstand the full output voltage plus the peak inverse voltage generated by switching in the transformer, which is typically several times the forward voltage. Also, the high voltage capacitors 14 are placed in series to enable operation at the required voltage, together with the resistors 15 in parallel with the capacitors help to balance the voltages across them. While only two windings 12 are shown on the output of the transformer for clarity, in practice this number may be higher. The preferred ranges for parameters of these components are 2 to 10.

The high voltage generator 6 provides this level of DC voltage to the pulse switching controller 7, which in turn applies this voltage to the probe electrodes 26 via terminals 27 in a controlled pattern for optimal electroporation treatment. This is described in more detail below.

Figure 4:
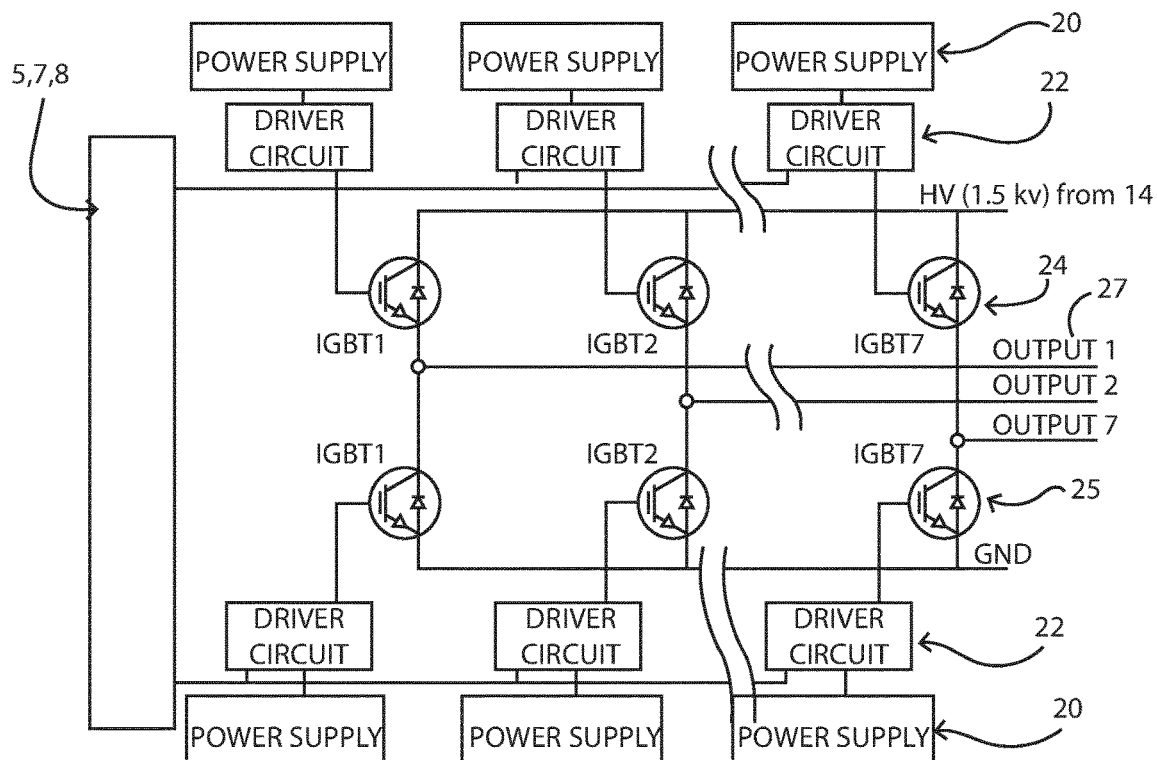
FIG. 4 shows a pulse switching and control block in detail.
Figure 5:
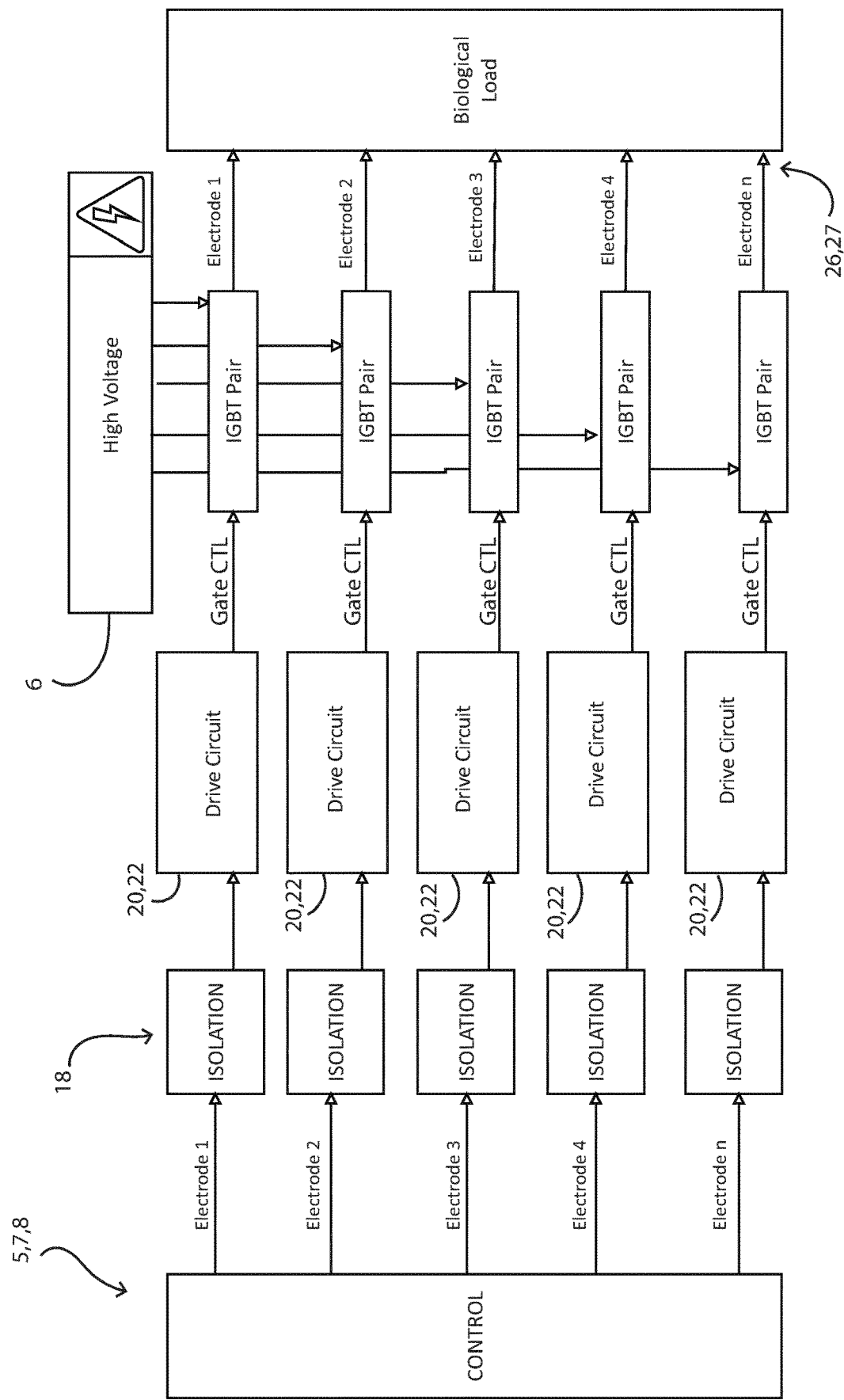
FIG. 5 shows the electrical power flow through to the biological load in use.

Referring to FIGS. 4 and 5 the pulse switching controller 7 and the voltage set and maintain circuits 8 are shown in more detail. Driver circuits 22 with independent floating power supplies 20 are individually addressable by the controller 5 so that IGBTs 24 and 25 deliver high voltage pulses to the probe 26 terminals 27, in which the polarity and duration of voltages supplied to the probes is optimized.

To achieve the necessary switching of the probes, the driver circuits 22 connect each probe 26 electrode to either the high voltage rail HV or to ground GND, and the voltage duration and polarity of a pin pair can be set in software. To achieve the high voltages required, Insulated Gate Bipolar Transistors (IGBTs) (or FETs in other examples) are used. For higher voltages the number of transistors may be increased. Only seven circuits are shown but the number of outputs can be increased or decreased as required.

As noted above, the pulse switching controller 7 comprises seven top driver circuits and seven low driver circuits 22 each with a dedicated link to the power supply 20 (primarily the capacitors 14 of the high voltage generator 6). There is a series of (in this example seven) pairs of IGBTs 24/25, each pair being for one probe electrode terminal 27. For example, the first (left-most in FIG. 4) IGBT pair 24/25 connects the first probe electrode P1 to either the high voltage from the rail HV or to ground GND. At the same time the second IGBT pair—probe electrode P2—would connect the opposite way to ground or the HV rail. Thus, a current is passed through the biological load in either direction.

At any one time one probe electrode has either a high or a low (+1.5 kV or −1.5 kV) and its opposed electrode is grounded. The fact that one electrode of a pair has a voltage of 1.5 kV less than the other gives a relative negative pulse. So, viewing a pair of opposed electrodes, the voltage is bipolar, the relative voltage switching from +1.5 kV to −1.5 kV.

The voltage set and maintain circuit 8 comprises a comparator device and an isolated control circuit which assures that the output voltage is maintained at the set voltage for the pulse train delivery.

Figure 6:
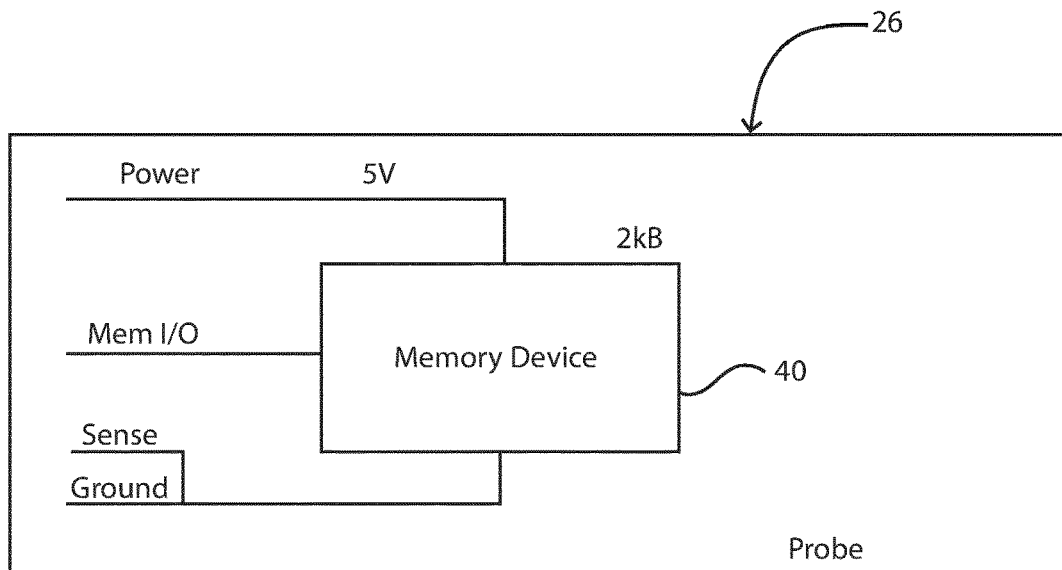
FIG. 6 is a diagram illustrating electrical aspects of a probe.

Referring to FIG. 6 the probe 26 has a memory device 40 storing the probe type, configuration, and output setting data. There is a single-wire memory I/O line to the memory device 50.

Figure 7:
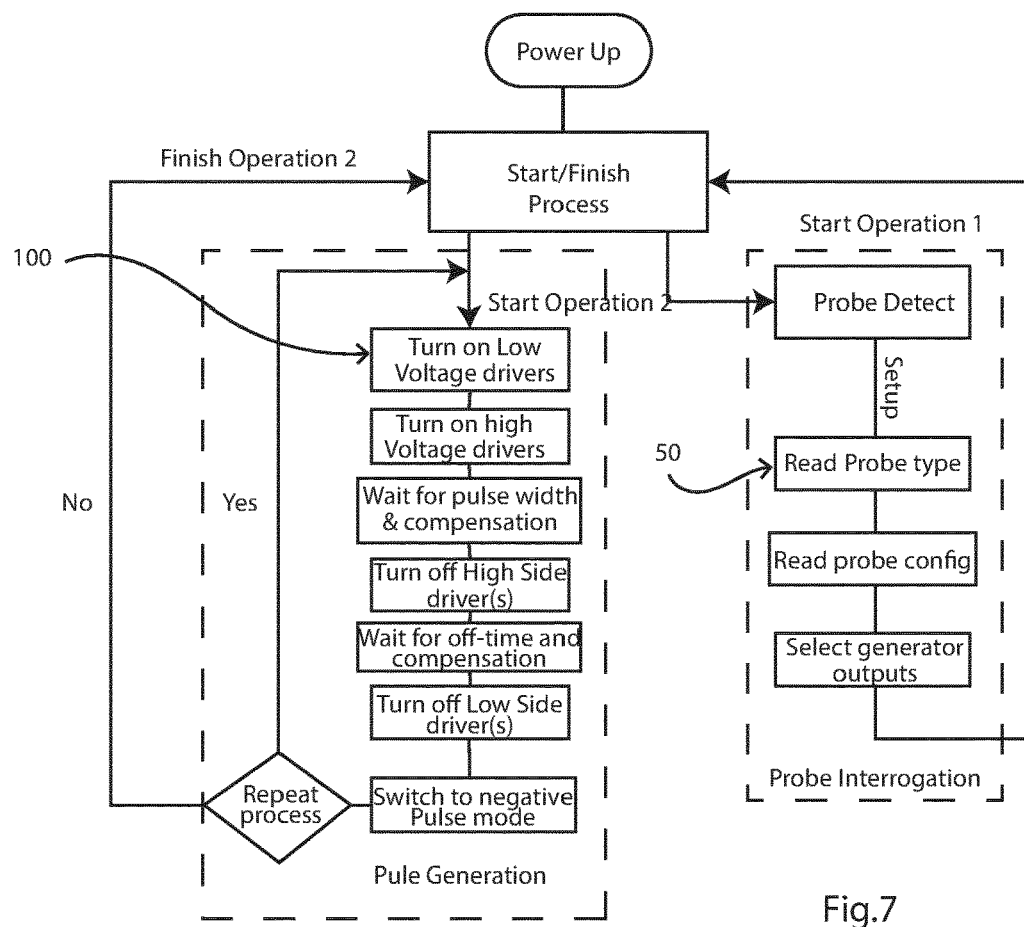
FIG. 7 is a flow diagram of a pulse generator algorithm implemented by the controller.

Referring to FIG. 7 a pulse switching control algorithm 100 is implemented by the controller 5 for the generation and application of the pulses. There is a Start Operation sequence 50 in which the probe 26 memory device 40 is read for the probe type, configuration, and output setting data. In the probe drive sequence 100 the low side drivers 22 are turned on, followed by the high side drivers 22. The controller waits for the required pulse width and compensation time and then turns off the associated high side driver 22. The controller waits for the off-time and compensation time and turns off the low side drivers 22. A negative polarity pulse can then be produced if desired.

Figure 8:
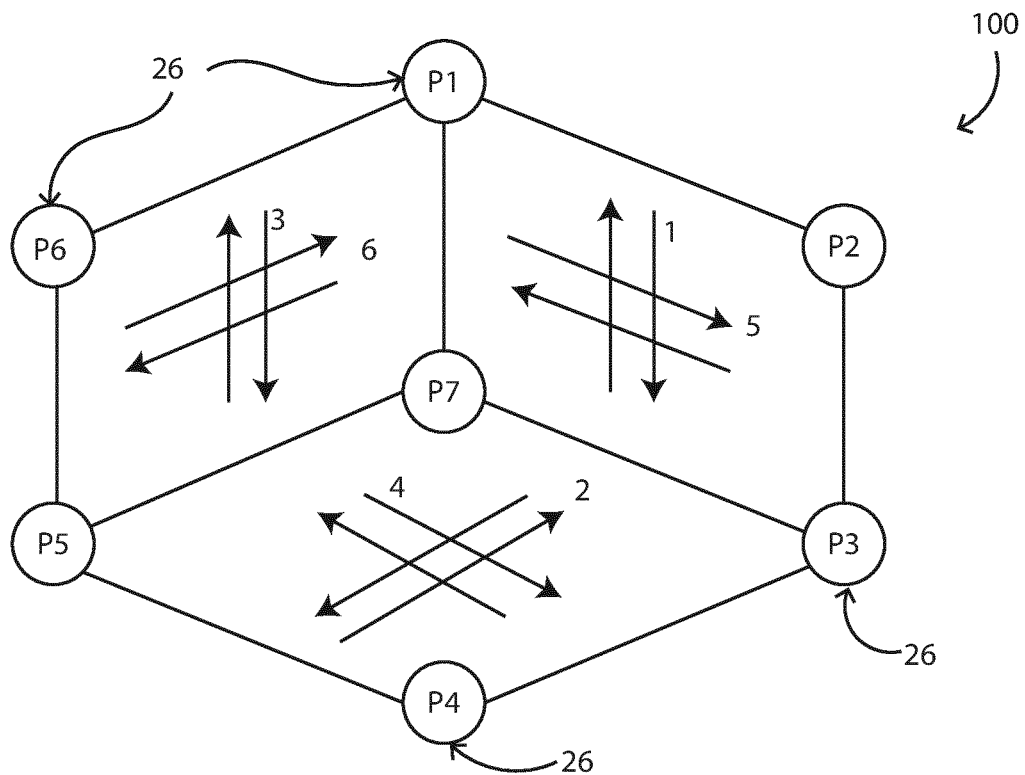
FIG. 8 is a diagrammatic representation of spatial application of voltage by the probe in a biological load.

The controller manages the control pulses to rotate the voltage source through 180° using a dual-pin probe contact technique, as shown in FIG. 8, in which the pin probe electrodes are individually labelled P1 through P7.

The switching controller 5 interrogates the probe 26 to initially verify that it is approved and discovers the permitted pulse profile intended for the particular application. The probe identity is assessed and the appropriate pulse profile and sequence is defined. When the probe 26 is plugged in, a sense wire actives the microcontroller by pulling the sense line low. The micro-controller can then communicate with the memory device 40 to read the probe parameters. Several copies of the parameters are stored in the probe memory 40 with error detection to verify a correct reading. The probe identity reading sequence as follows:

Sense probe attached
Communicate with memory device and read first set of parameters
Verify error detection codes
If verified, setup complete
If not verified, read next block of parameters
Verify error detection codes
If no good parameter set found create error message
Indicate probe type on screen as visual indication to user.

Referring again to FIG. 8, rotation of the voltage pulses as illustrated results in comprehensive electroporation of the affected tissue. In this scheme, the electrodes are energised in pairs and with manipulation can arrange the orientation of the pulses in a controlled manner Electrodes P1 and P2 are made positive (linked to HV via top IGBTs 24) and electrodes P7 and P3 are made negative (linked to GND via bottom IGBTs 25) giving a field marked 1 in FIG. 8. Reversing the polarity of the pairs (i.e. P1 and P2 negative and P7 and P3 positive) gives the opposite field. Making electrodes P1 and P7 positive and electrodes P2 and P3 negative gives a field marked 5 in FIG. 8 traversing the field marked 1. Again, reversing the probe polarities gives the opposite field. And so on for the other possibilities.

Cancer cells display characteristic fractal patterns, with a solid tumour consisting of millions of these cells. The geometric shape of a solid tumour can be modelled as an ellipsoid ranging from oblate to prolate. Whilst small tumours can be treated in a single run at a single position, for tumours where its size is larger than the distance between the electrodes it is necessary to rotate electrodes around the tumour surface in order to maximize cell permeabilization and subsequently the treatment. The apparatus described here gives a usability and efficiency advantage, in that the number of probe repositioning steps are reduced due the electrical field being rotated around the tumour surface by the apparatus.

Additionally, there is a clinically efficacious advantage due to the delivery of electric field homogeneity in multiple directions across the tissue from a single position, increasing the probability of cell membrane poration, thus maximizing treatment effect from chemotherapeutic drugs such as bleomycin and cisplatin, or with other therapeutic combinations such as calcium, potassium and gene therapy.

Also, it is important to note that for optimum treatment efficacy, it is necessary to deliver pulses during the pharmacokinetic peak. This apparatus reduces the number of times that the electrodes need to be repositioned and, as such, the time to deliver pulses across the entire tumour surface. As described in more detail below with reference to FIGS. 19 and 20, additionally the delivery of a substance such as a therapeutic agent directly via the electrode being used via pores along its length help optimally ensure its correct and efficient delivery.

Additionally, more gentle field conditions can be used because these fields can rotate around the tumour surface.

The scheme illustrated in FIG. 8 is based on at least four probe electrodes arranged in a quadrangle and so defining a space in the transverse plane between them. Two electrodes defining one side of the quadrangle are positive (for example P1 and P7) while the two electrodes (for example P2 and P3) defining the opposed side are negative, and this state is immediately reversed. It is then performed in the orthogonal direction (for example P7 and P3 positive, P1 and P2 negative). The same patterns are repeated for the other quadrangles defined by the electrodes P1-P6-P5-P7 and by probes P5-P7-P3-P4). Of course, many of the electrodes play roles for different quadrangles.

The effect of this scheme is that the tissue between the electrode 26 is grouped into three zones bounded by the quadrangles, each of which is comprehensively treated with four approximately orthogonal charge directions through the tissue, as indicated by the arrows within the quadrangles in FIG. 8.

In general terms the controller is configured to simultaneously drive a first group (e.g. P1, P7) of probe terminals 27 with the same potential (e.g. 1.5 kV) and an opposed second group (e.g. P2, P3) with a different potential (e.g. ground), for application of a charge across and between a plane (e.g. orthogonal) defined by the first and second probe locations. As the apparatus 1 is for driving an external set of probes, it is programmed to drive the terminals 27 with pre-setting of the probe locations. This pre-setting may be referred to as mapping data, which can take the form of a series of instructions for the driving scheme, or it may indicate the physical locations. This pre-setting may arise from the interrogation of the probe and/or from user inputs.

The controller advantageously immediately reverses the direction across the plane, with the first group being applied with the potential previously applied to the second group and vice versa, in which the first and second groups are re-defined so that charge is applied in one direction across the space and then immediately reversed. Also, the controller, after reversing the direction across the plane, then drives third and fourth groups (e.g. P1, P2 and P3, P7) which also define the plane but the direction between the third and fourth groups is different from that between the first and second groups, in one example approximately orthogonal as shown by the arrows within the quadrangle of P1-P2-P3-P7 for example.

Another advantageous aspect of the electroporation scheme is that for driving a pulse to one pair of probes there is a ramp-up, plateau, and a ramp-down sequence. Each of the ramp durations is less than 0.5 µs and typically less than 0.25 µs due to the short turn-on time of the switches used and the fact that they are driven by individual driver circuits 22, each dedicated to an individual switch and each being individually addressable by the controller. Hence if there is a minimum duration of say 2 µs needed for each pulse for treatment purposes, the overall duration required is only 2.5 µs, upon which the direction is immediately reversed. Hence in an overall period for one axis through the tissue, there is a total 5 µs duration for both directions at 180°. By switching direction by 180° so quickly there is optimum treatment with minimal patient discomfort caused by muscle contraction. This will in many cases avoid need for a general anaesthetic for treatment of for example skin cancer. For improved outcomes the pulses can also be produced orthogonally across the tissue in both directions, again with a duration of 5 µs.

Figure 9:
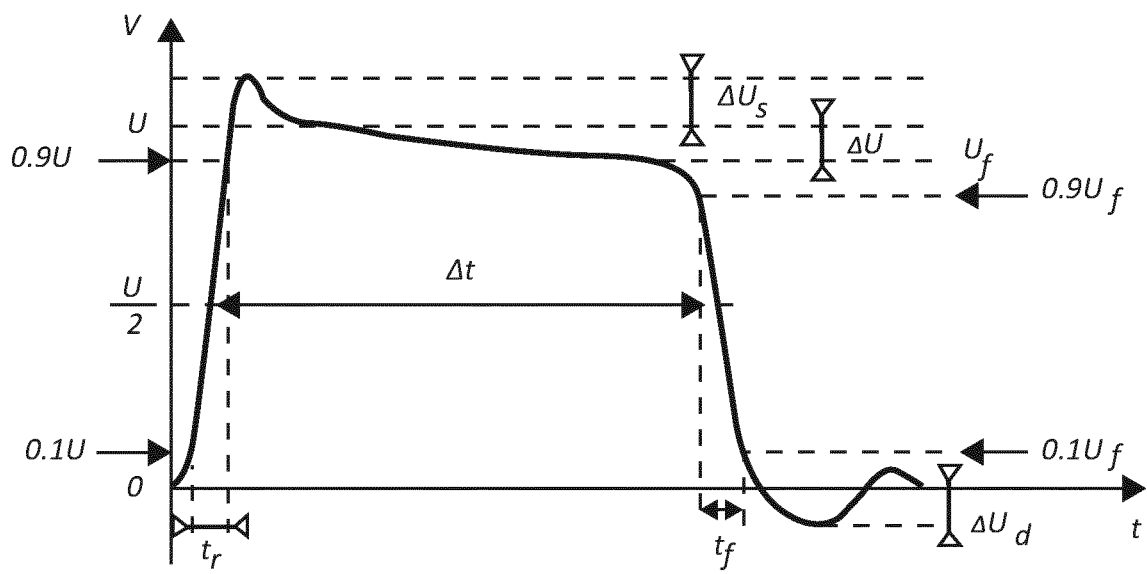
FIG. 9 is a diagram of the electroporation pulse delivered by the generator, the parameter values of which are set out in Table 1 below.

Referring to FIG. 9 the main parameters for a drive pulse are indicated. In these examples the values for these parameters are as follows.

TABLE 1

| Parameter | Example 1 High Frequency Probe to 100 Ohm resistor configuration | Example 2 High frequency probe to potato tissue, needle electrode, 5 mm depth, 5 mm separation | Example 3 High frequency probe to potato tissue, needle electrode, 10 mm depth, 10 mm separation. |
|---|---|---|---|
| U (plateau) | 980 V | 1005 V | 1005 V |
| $t_r$ (ramp up) | 68 ns | 460 ns | 360 ns |
| $t_f$ (ramp down) | 48 ns | 920 ns | 920 ns |
| $\Delta U_s$ | <1 V | <20 V | <1 V |
| $\Delta t$ @ U/2 | 2.060 µs | 2.140 µs | 2.040 µs |
| $\Delta t$ @ U | 1.940 µs | 1.4 µs | 1.66 µs |
| Pre-Impedance | | 552 Ohms | 734 Ohms |
| Post-Impedance | | 444 Ohms | 643 Ohms |

In the table above, example 1 is preferred. Examples 2 and 3 are examples of different electrode configurations, with different depth and separations spacing distances as outlined in the table. These differences in electrode configuration results in higher ramp durations. As noted in extreme cases, the ramp down values can approach 1 µs, although this is generally not preferred, it is preferred that the ramp durations be less than 0.5 µs.

Referring to FIG. 10 an image capture of representative pulses of a pair of opposed electrodes taken during the experiments included in Table 1—1000V, 2 µs bipolar pulse. $\Delta U_s$ is not visible on this image due to the position of the electrodes and the impedance of the potato tissue. There is a minor delay of less than 1 µs present due to dead time in order for one transistor pair to turn off, before the other ones turn on (preventing a direct short through the system). The circuit design is such that it minimises this dead-time. The oscilloscope shows the bipolar pulses (+1000V, −1000V) in which the rise time and the fall time are sharp and the electroporation pulse amplitude stays at the expected level for the pulse duration. The features (U, tr, tf, U/2) of FIG. 9 can be identified in this image.

It will be appreciated that the multistage transformer approach and output switching delivers high-voltage/high-current and flexible polarity control, in a compact housing. It also has integrated probe detection and automatic parameter setting to ensure safe delivery of application-specific doses.

The switch-mode transformer 11/12 operates efficiently at low voltages but in high voltage applications they tend to suffer design trade-offs. This problem is avoided in this invention by virtue particularly of;

The use of a transformer drive circuit, designed for low dead time losses across a wide range of operating conditions and part to part variations The use of n secondary windings in series to deliver a predefined voltage Vout through a modular circuit Vmod, where Vout=Vmod*n.

The selection of transformer core material and winding material

The use of a feedback circuit (8) to monitor and maintain this voltage

It will be appreciated that the apparatus generates safe and effective high-voltage pulses with accurate and reliable control of the pulse profile; time, duration, polarity and orientation. This is particularly advantageous at ensuring that there is effective treatment without causing burning or need for unwanted level of anaesthetics. The level of control is also contributed to by the sensing of the connecting probe to ascertain its permitted operating parameters and configuration of the generator parameters automatically. It is particularly advantageous that the apparatus performs machine-initiated interrogation of the probe to verify compatibility and select appropriate pulse generation profile from an internal lookup table.

Also, in other examples the controller 2 may generate a research interface screen that provides access to more pulse configuration setting options made available under controlled circumstances. This allows researchers to vary the pulse parameters up to the maximum allowed for the probe, to investigate optimal parameters.

Example Uses of the Apparatus

The apparatus as described above may be used for various methods of treatment, either irreversible electroporation or reversible electroporation. Some of these methods may be performed with other electroporation apparatus known in the field, provided they can provide the electrical parameters indicated.

As noted in the introductory passages in the beginning of this specification, electroporation is a medical and molecular biology technique in which an electric field is applied to cells or molecules in order to increase the permeability of the cell membrane, allowing chemicals, drugs, or DNA to be introduced into the cell. Electroporation has a number of possible medical fields of application, and can be used both reversibly and irreversibly. In a typical electroporation process, short and intense electric pulses are generated to transiently permeabilize the cell membrane.

In reversible electroporation, which may be used in relation to for example chemotherapy, the electric field is below an electric field threshold and allows the cell membrane to repair after the treatment. Reversible electroporation may involve allowing a molecule, such as a drug or gene, into a cell or molecule that is normally not permeable for this substance without inducing cell death. The electric field threshold for a cell is individual for the cell.

In irreversible electroporation (for cell ablation) the electric field is greater than a particular electric field threshold, which creates permanent nanopores in the cell membrane, disrupting the cellular homeostasis and consequently forcing the cell to enter an irreversible cell death pathway such as via apoptotic or necrotic mechanisms.

We describe methods of electroporation, comprising the steps of inserting probe electrodes into a biological load and applying voltage pulses into the electrodes and the load for electroporation, and preferably, the controller applies the pulses of opposed probe electrodes in a bipolar manner.

Preferably, the pulse plateau (U) duration ($\Delta t$) is in the range of 1 µs to 5 µs, preferably 1 µs to 3 µs. Preferably, the pulse plateau voltage amplitude (U) is in the range of 100V/cm to 3000V/cm, preferably 500V/cm to 2000V/cm. Alternatively the individual pulse length may be in less than 1 µs and in the 0.03-0.99 µs range with the pulse plateau voltage amplitude (U) in the range of 5 KV/cm to 50 KV/cm, preferably 10 KV/cm to 20 KV/cm.

Preferably, the energized on-time duration of active treatment, in which the probe electrodes are pulsed, is in the range of 100 µs to 300 µs, and the bipolar pulse frequency based on a cycle of two successive pulses is in the range of 100 kHz to 500 kHz.

The electrodes may be driven so that current flow in the probe electrodes and the biological load is less than 500 mA for migration of DNA into permeabilized cells.

In some examples, there is irreversible electroporation in which a substance such as a liquid solution such as an hyperosmotic solution is injected to the site to assist a process of cell ablation, and said solution may include Calcium or potassium. Preferably, Calcium ions (Ca++) are injected directly into tissue at a concentration in the range of 2 mMol/L to 250 mMol/L and preferably in the range of 2 mMol/L to 150 mMol/L.

The composition of the substance may be chosen at least in part to cause a desired level of tissue conductivity adjacent and between the electrodes. For example, the substance may include de-ionised water for reduced conductivity. Alternatively or additionally, as described in more detail below with reference to FIGS. 15 to 18, the substance may include a foam solution which preferentially elevates the resistance (Ohms) within the tissue environment in contrast with a more conductive liquid solution. As a result, the current (Amps) generated during delivery of the electroporation pulses is reduced in tissue where a foam solution has been injected, allowing for a safer and more effective treatment to be achieved.

Injection of a Substance

A solution comprising calcium ions (Ca++) with a concentration of between 2 mMol/L to 150 mMol/L may be injected for transient permeabilization by electroporation with an applied pulse voltage of 800 V/cm and 2000 V/cm; a pulse plateau duration of 1 µs to 3 µs, and a pulse number in the range of 1000 to 10,000. A solution with calcium ions is just one example. Others are given below.

In one example, there is delivery of DNA to cells in reversible electroporation in the steps of:
(a) injection of the DNA to the site,
(b) insertion of the probe electrodes,
(c) driving pulses to the electrodes to permeabilize the cells, said driving being bipolar pulses at a frequency in the range of 100 kHz and 500 kHz for example; a pulse plateau duration in the range of 1 µs to 5 µs and preferably 1 µs to 3 µs; and a voltage amplitude in the range of 100V/cm to 3000V/cm; and
(d) low frequency electrode driving to draw the DNA or agent into the cells in an electrophoretic phase low-voltage pulses of less than 5V for a pulse duration of 10 ms to 100 ms.

In one example for DNA delivery there is:
injection of the DNA to the site, and/or
delivery of one or more monopolar 800V/cm to 1600V/cm pulses, then treatment with bipolar HF a frequency in the range of 100 kHz and 500 kHz for example; a pulse plateau duration in the range of 1 µs to 5 µs and preferably 1 µs to 3 µs; and a voltage amplitude in the range of 100V/cm to 3000 V/cm, and/or
delivery of one or more 1V/cm to 200V/cm monopolar pulse.

The monopolar pulse(s) for the higher voltage of 800V to 1600V may have a pulse duration in the range of 50 µs to 250 µs, preferably in the range of 100 µs to 200 µs. The voltage is more preferably in the range of 1000V/cm to 1200V/cm.

The monopolar pulse(s) at the lower voltage of 1V/cm to 200V/cm may have a pulse duration of 10 ms to 10 s, preferably 20 ms to 100 ms. This voltage is preferably in the range of 100V/cm to 150V/cm.

The second monopolar pulse(s) is preferably delivered within is of the first monopolar pulse(s).

In one example, a drug is injected into the site and electroporation takes place for migration of the drug into the cells to cause cell ablation, for example chemotherapy agents.

In one example, the controller, after pulsed driving of the electrodes, discharges stored charge in a pulse of near zero duration followed by exponential decay.

Opposed electrodes are inserted into the biological load at a separation of 1 mm to 30 mm, more preferably 1 mm to 10 mm, and more preferably 2 mm to 8 mm. The probe electrodes may be needle electrodes, but not necessarily.

The controller of the electroporation apparatus which is used is programmed to provide high frequency operating parameters in the following ranges.

The pulses of opposed probes or electrodes are preferably bipolar.

The frequency (bipolar frequency, a cycle being both a positive pulse and a negative pulse) is preferably in the range of 100 kHz to 500 kHz. This is termed "high frequency" in this specification. This corresponds to a pulse length (plateau) of about 1 µs to 5 µs, but for many uses the range is more preferably in the range of 1 µs to 3 µs, and more preferably about 2 µs.

The voltage amplitude is in the range of 100V/cm to 3000V/cm, and preferably about 800V/cm to 2000V/cm. Electroporation pulses can be effective where there is a hyperosmotic solution or foaming agent, as detailed below.

The duration of active treatment, in which the probe electrodes are pulsed is preferably in the range of 0.1 ms to 1 s, more preferably 0.2 ms to 10 ms.

The pulses are delivered in bursts of duration (energised one time) in the range of 100 µs to 300 µs within this duration. For example if the pulse length is 2 µs there will be about 25 to 75 pulse cycles for the energised on time.

The current in the probes is less than 1 A, preferably less than 500 mA. However, current is a derived value, depending on the biological load. It is more preferred that it be lower than about 500 mA for DNA migration into cells, but is less important for other methods. In some examples the current when delivering the high frequency pulses may be in the range of 5 A to 40 A. For DNA delivery the applied voltage to is preferably less than 5V and the current would be less than 1 A.

Where an agent is provided in the site it is by any well-known injection technique.

Liquid Injection: Hyperosmotic Treatment for Cell Ablation

A liquid solution injected locally to the target tissue aids irreversible electroporation and cell death, and enables lower voltage pulses to be effective in the high frequency drives outlined above. Such solutions may for example include Calcium ions to induce cell death.

In one example Calcium ions (Ca++) are injected intra-tumourally at a concentration in the range of 2 mMol/L to 150 mMol/L and preferably at the bottom end of this range due to the high frequency drive outlined above.

Liquid Injection: DNA Delivery (Reversible Electroporation)

For reversible electroporation there is:
(a) Injection of the DNA to the site.
(b) Insertion of the probe.
(c) High frequency treatment according to the high frequency parameters above, to permeabilize the cells. This is termed an electroporation phase.
(d) Low frequency treatment to draw the DNA into the cells. This is termed an electrophoretic phase. In this phase there are low-frequency low-voltage pulses of less than 5V for a pulse duration of 10 ms to 100 ms. This achieves effective uptake of the DNA into the cells, primarily due to the DNA negative charge.

Liquid Injection: Drug Delivery

A drug is injected into the site and electroporation takes place to enable intracellular passive diffusion of the drug. In one example the drugs are chosen to cause cell death (ablation), for example chemotherapy agents. The passive diffusion of the chemotherapy agent is enabled by the effect of the high frequency electroporation and leads to cell death. For example, the drugs may be Bleomycin or Cisplatin.

In general, for drug delivery, unlike for DNA delivery, there is no low frequency stage ((d) above).

Referring to FIGS. 11 to 13, these illustrations show:
Effect of high frequency vs. standard low frequency electroporation pulses on potato tissue,
Effect of high frequency electroporation vs. standard low frequency (pulse length of about 100 µs) in a murine tumour model when combined with drugs, and
Reduced muscular contractions due to high frequency electroporation.

The data of FIGS. 11 to 13 clearly demonstrates effective results at clinically manageable voltages (<1500V) enabling drug, ion and DNA absorption.

FIG. 11

Healthy biological tissue exhibits a different electrical impendence from abnormal and pre-cancerous tissue i.e. current flows more easily across abnormal and pre-cancerous tissue, and as such the measured impedance is lower than healthy biological tissue.

The tissue impedance and changes in tissue impendence may in some examples be measured by the apparatus across a frequency spectrum. This allows the controller to automatically modify its operation and to generate user information to for example distinguish abnormal and pre-cancerous tissue from healthy tissue. This is done during treatment before a pulse is delivered and after a pulse is delivered, delivering diagnostic capability and can provide the treating health care professional with actionable feedback on the areas which have been treated and are to be treated. It also allows the controller to automatically adjust the voltage level to ensure that the current is not excessive, thereby automatically avoiding adverse effects of significantly reduced impedance.

The controller measures the impedance by applying an AC signal to the tissue over a suitable frequency spectrum, typically from 1 kHz to 100 kHz. This is done immediately before and/or immediately active high-frequency electroporation driving.

FIG. 11 shows the effect of high frequency (2 µs bipolar (about 217 KHz) vs. low-frequency (100 µs monopolar (1 Hz), 70 µs monopolar (1 Hz) electroporation pulses on Potato tissue. It illustrates tissue impedance as measured using a potato tissue model. A pair of probe needle electrodes were inserted 0.4 cm apart and the tissue impedance pre and post electroporation delivery was measured (experiments conducted in triplicate).

Impedance changes were monitored using the following parameters:
2 µs bipolar (about 217 KHz) energized time of 200 µsec (50 pairs) delivered 50 times @1000V/cm
100 µs monopolar (1 Hz) delivered 8 times @1000V/cm
70 µs monopolar (1 Hz) delivered 90 times @1500V/cm Changes in tissue impedance are caused by the opening of ion gates and release of electrolytes into the surrounding tissue after electroporation pulses. It provides an indication of the degree of electroporation. The largest delta change occurred with the irreversible electroporation parameters of group C (right hand plots) with a change of 130 followed by group A (left hand plots) with a change of 118. Standard electroporation parameters as a control for drug delivery (Group B) (middle plot) provided a net change of 72. The data indicates the degree of tissue electroporation achieved with the bipolar high frequency parameters which occurs despite the high frequency delivery and the observed decrease in muscular contractions. This data indicates cell permeabilization, in which the left-hand plot shows that the high frequency operation of the apparatus achieves good permeabilization while avoiding risk of patient discomfort due to the high frequency operation.

FIG. 12

FIG. 12 shows effect of high frequency (217 KHz, 2 µs pulse plateau) electroporation vs. low frequency (1 Hz) in a murine tumour model when combined with drugs.

Preclinical testing carried out with the apparatus 1 using a mouse tumour colorectal model is shown. Tumours were grown in mice up to 0.1 cm$^3$ and then treated. Four groups were studied with 6 mice in each group:

A) Control group, no treatment.
B) ECT (electrochemotherapy) Control
C) ePORE (apparatus 1) with Bleomycin, and
D) ePORE (apparatus 1) with Calcium.

ECT Control (B): Standard electroporation parameters with bleomycin (250 IU) injected directly and using a total of 8, 100 μs polar pulses delivered at 1 Hz with an applied field of 1000V/cm.

ePORE Bleomycin (C): The pulses delivered as a bipolar pulse at a frequency of 217 KHz. Bleomycin (250 IU) was injected directly.

ePORE Calcium (D): As above for ePORE bleomycin but using calcium injected intratumourally at a concentration of 9 mg/ml and pulses delivered as a bipolar pulse at a frequency of 217 KHz.

The short ramp times (<0.25 us to 1000V) enables more efficient uptake of large macromolecules and ions (including Ca++) directly across the cell membrane with the higher frequency allowing for more homogenous electrical field penetration through the cell membrane.

In one example uptake of DNA was achieved across the cell membrane utilising high frequency (>200 KHz) bursts in combination with low current (<1 Amp) pulses. A bipolar square wave high voltage high frequency burst of 1-2 μsec length bipolar×50 (energised on time of 100-200 μs) followed within one minute by a unipolar square wave low voltage low current pulse of less than 5V<250 μAmps for 1-10 m duration.

The apparatus results in enhanced DNA endocytosis and uptake leading to improved cell transfection and DNA expression.

In another example cell death is achieved through delivery of the high frequency electrical pulses (>200 kHz) when delivered into a hyperosmotic solution. Such a solution could be prepared from Sucrose, Glycerol, Xylose, Mannitol or Fructose at a concentration of between 125 and 300 mMol/L. Such a solution could also include up to 99 mMol/L Ca2+ or Mg2+ or K+.

In another example, a solution comprising calcium ions (Ca++) with a concentration of at least 2 mMol/L in which the transient permeabilization is made by electroporation by 500-1500 V/cm; pulse length 0.1 μs-3 μs; pulse number 1000-10,000; and pulse frequency 200 kHz to 500 kHz.

FIG. 13

This diagram shows reduced muscular contractions due to high frequency electroporation by the apparatus 1. Accelerometer data was calculated from porcine tissue when electroporation was delivered to colorectal tissue. Muscular contractions were observed when using 1000V 2 μs bipolar pulses with a gap of less than 0.5 μs between each pulse (about 217 kHz); using 1000V 2 μs bipolar pulses with a gap of 2 μs between each pulse (125 KHz); using 100 μs monopolar pulses at 1000V (1 Hz) and using 100 μs monopolar pulses at 1500V (1 Hz). Peak acceleration observed at 217 kHz was 0.04 g; @125 Hz was 0.08 g; @1000V 100 μsec was 0.75 g; @1500V 100 μsec was 0.83 g.

FIG. 14

As noted above the apparatus drives a pulse to one pair of probe electrodes with a ramp-up, a plateau, and a ramp-down sequence. Each of the ramp durations is less than 0.5 μs or preferably less than 0.25 μs due to the short turn-on time of the switches used and the fact that they are driven by individual driver circuits 22.

Figure 14:
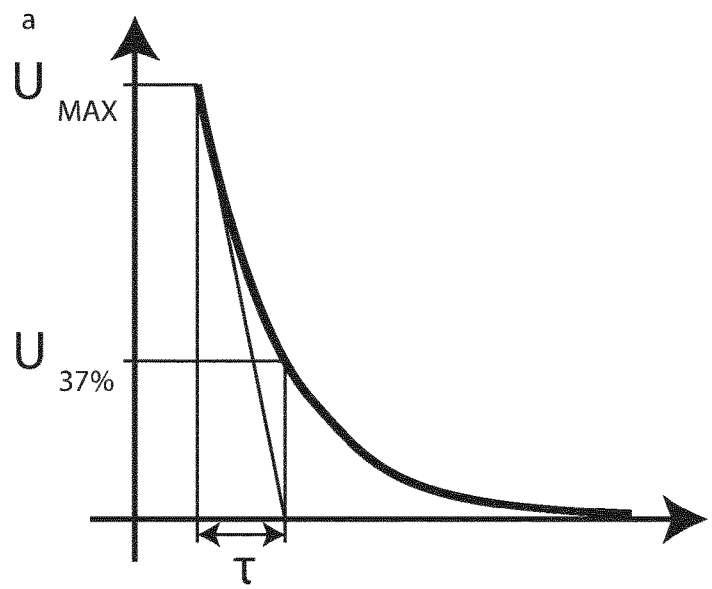
FIG. 14 is a plot for a pulse waveform of one example.
Figure 15:
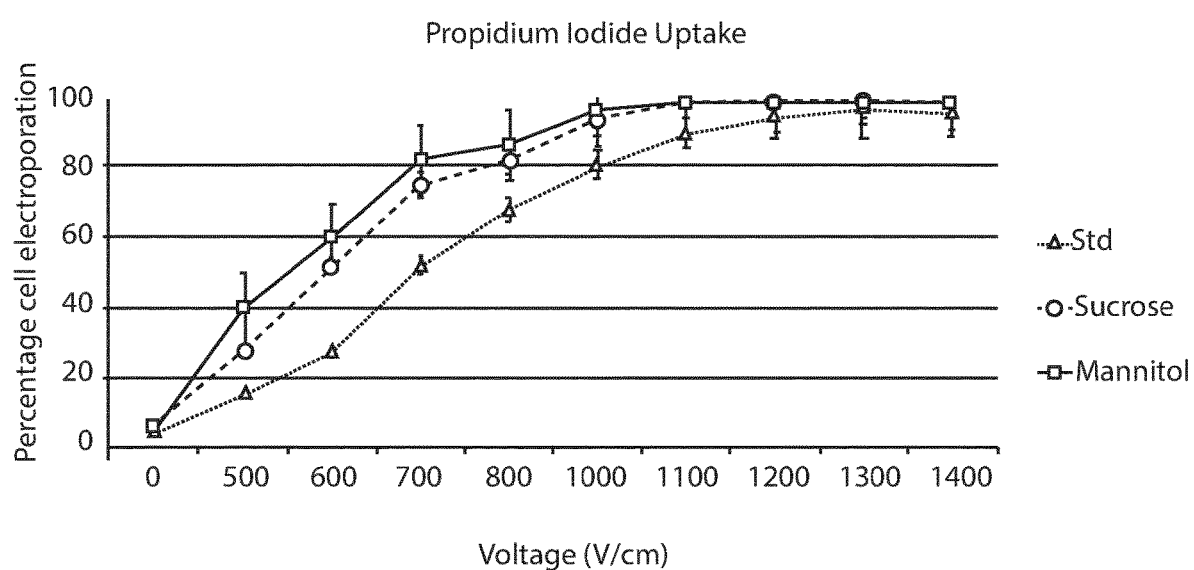
FIG. 15 is a plot of propidium iodide uptake with electroporation.

In a variation the controller drives at least some pulses with a ramp-up as described above, however the plateau is set to 0, before turning off the switches to achieve the pulse, thereby achieving an exponential decaying pulse. The capacitors are charged as normal and then the pulse is activated, letting it discharge freely. The decay rate as shown in FIG. 14 is controlled by the value of the balance resistors 15 and the capacitors 14. Thereby, the controller drives the electrodes to an amplitude of $U_{max}$ and then turns off the pulse—i.e. sets the pulse duration to 0. Hence, the electroporation apparatus for some of the treatment time drives the pulses with a decaying exponential shape.

This operation may be of benefit after high frequency operation. It effectively discharges the capacitors

FIG. 15

Flow cytometry using a propidium iodide marker was used to determine the relationship between electroporation effectiveness/cell permeabilization and the medium used as a buffer for the cells.

We assessed the use of electroporation with ultrashort bipolar pulse lengths (2 μs) to induce cell permeabilization across a range of field strengths (V/cm) using a standard isotonic buffer (≠270 mOsm/l) and hyperosmotic buffers containing Mannitol or Sucrose (~600 mOsm/l).

The field strength (V/cm, the distance being the separation of the electrodes) was adjusted from 500V/cm to 1400V/cm at 100V intervals and a determination made on the degree of PI uptake and consequently cell permeabilization.

To assess the efficacy of electroporation delivered to cells in vitro using the ultra-short pulses, we utilised a flow cytometer (FacsCalibur™, Becton Dickinson, USA) and the flurochrome, propidium iodide (PI), which only fluoresces once bound to DNA. Due to its size, viable cell membranes are impermeable to propidium iodide and therefore its entry into electroporated cells and subsequent fluorescence upon binding to DNA within the nucleus can be detected. The FacsCalibur™ apparatus has the capacity to quantify fluorescence in individual cells, which varies depending upon the efficacy of electroporation (i.e., number of pores open in the cell membrane due to electroporation—allowing entry of PI into the cell nucleus, resulting in detectable fluorescence from the cell).

The FACSCalibur™ flow cytometer with CELLQUEST™ software was used for analysis of cell size and fluorescence. Cell samples were obtained during the completion of the electroporation experiments. In brief, the measured ratio of electroporated to non-electroporated cells was calculated as follows. The 'Collection Criteria' were set at the position of 'Event Count or Time' in the Acquisition and Storage dialog box and the acquisition time was selected. The flow rate was set and the "Voltage", "Amps gain", and threshold were adjusted to ensure that the cells could be detected. Forward scatter (FSC) and side scatter (SSC) were collected in linear mode and FL2 (PI Fluorescence) set in log mode. Acquisition of data could not start until the sample voltage became stable. A total of 10,000 sample points (cells) were collected per data point. The FSC versus FL2-H contour plot of the negative control (cells not electroporated) served to define three regions: representing intact cells, cell membrane permeabilized cells, and nuclear membrane permeabilized cells. The remaining events at low channel number were scored as debris.

Foam Injection

The substance may be in the form of a foam, being a liquid with very small bubbles of a gas. A foam may be used to enhance the permeabilization effect of electroporation, with particularly beneficial results for high frequency electroporation (greater than 100 KHz). Use of a foam is described in more detail below. In this specification the relative concentrations of liquid and gas in the foam are expressed by volume at atmospheric pressure, such as in a syringe when loaded with air and liquid.

The foam may be formed by any suitable means, and indeed it may be done manually by the clinician in a syringe.

A major benefit of utilising a foam for direct injection into the target tissue to be electroporated is that it can act as a carrier if required for the molecule of choice while its impact on tissue conductivity relative to a liquid is superior in that it minimises increases in the conductivity. The air or gas component of the foam bubbles have minimal conductivity relative to a liquid and enable a more favourable environment particularly in the case of high frequency (>100 kHz) pulses, minimising the current delivered and aiding in enhanced cell permeabilization.

The use of high frequency (>100 kHz) bipolar electrical pulses are advantageous for direct cell ablation or cell permeabilization for passive diffusion of molecules. The combination with a foam in some examples confers a benefit to the efficacy of the procedure (relative to using an equivalent liquid solution).

Figure 16:
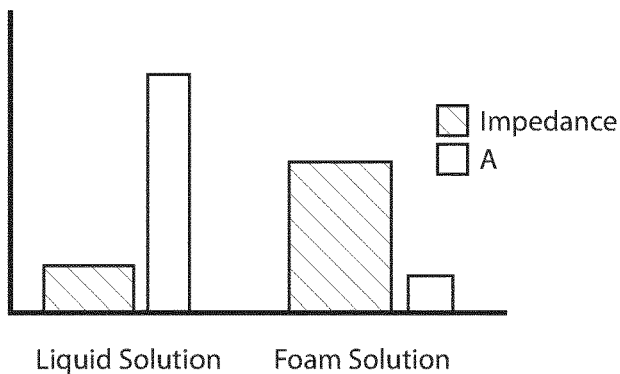
FIG. 16 is a plot indicating impedance and current in tissue with an injected liquid solution, compared with an injected foam solution.

FIG. 16 shows the impedance and current comparisons using a liquid compared to a foam. A liquid has a lower impedance (higher conductivity) and results in a higher current (A) delivered. On the other hand, a foam has a higher impedance/resistance and lower conductivity, resulting in a lower current (A) delivered. Where a foam is used the pulse width may be in a range wider than described above, in some cases in a range as low as 0.05 µs, and the voltage may in some cases be greater than 10 KV/cm.

Figure 17:
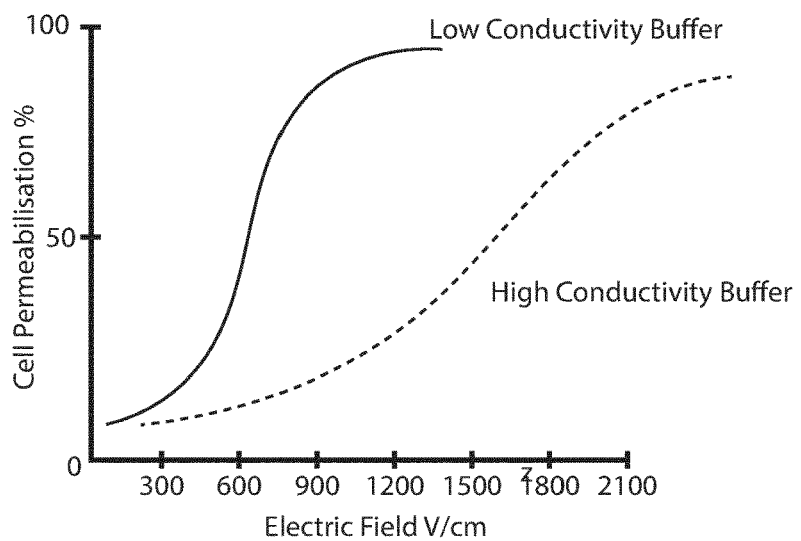
FIG. 17 is a plot of cell permeabilization vs. electric field strength for low conductivity buffer and a high conductivity buffer.

One example, FIG. 17, shows cell permeabilization from 0% to 100% when increasing the electrical field applied (V/cm). With the low conductivity buffer, the cells are permeabilised at a lower electrical field strength compared to the high conductivity buffer. It is our understanding that the foam will create a lower conductivity around the cell than if the corresponding liquid solution had been used.

Figure 18:
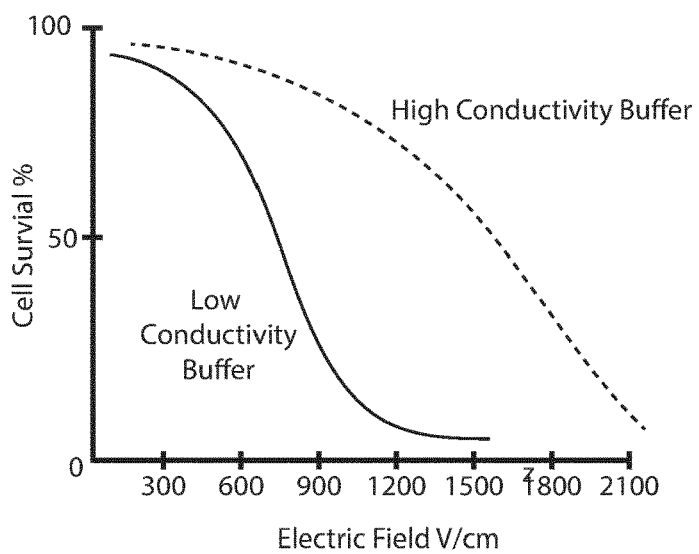
FIG. 18 is a plot of cell survival vs. electric field strength low and high conducting buffers.

FIG. 18 shows expected cell survival against increasing electrical field (V/cm). Low conductivity results in cell death occurring at a lower field strength compared to the high conductivity buffer.

Non-foamed liquid when injected is rapidly diluted by the circulating blood volume. The interaction with blood decreases the efficacy of the liquid solution, due to binding with plasma proteins that ultimately reduces the number of active molecules. A foam on the other hand, is able to displace blood rather than mixing with it, increasing the contact time of a higher concentration of active agent with the tissue and thus resulting in greater efficacy. With foam, a lower concentration of agent can be used to obtain the same therapeutic effect as in their liquid counterpart, reducing the prevalence of side effects associated with higher concentrations.

A foam, due to the presence of bubbles of a gas such as air, is less conductive than the corresponding liquid solution and consequently results in lower currents, higher cell permeabilization and less pain sensation for the patient.

Foam may in some examples be created by mixing albumin, gas, and a liquid solution, for example in a ratio of 1:4:1 by volume. Preferably, the ratio of gas (room air or $CO_2$ gas for example) to liquid is in a range of 1:2 to 1:10 by volume.

Preferably, the foam used includes one or more of the following:

Albumin, human serum albumin; concentration 10-50% preferably 15-30% by volume

Polidocanol (0.5-5% by volume) or Sodium Tetradecyl Sulfate (STS) (0.5-5% by volume).

STS and Polidocanol are sclerosing agents individually, whereas Albumin is not Polidocanol is also a local anaesthetic.

Albumin is a foaming agent solely whereas Polidocanol and STS are both foaming and sclerosing agents (they are an irritant and induce cell death directly).

Active agents (the molecules being introduced) in solution may include one or more of:

Calcium ions, $Ca^{++}$ (2 mMol to 150 mMol); Potassium (2 mMol to 100 mMol); Bleomycin; Cisplatin; DNA; and/or RNA.

Preferably, the electroporation pulses advantageously have parameters as follows:

bipolar pulses 0.05 µs to 5 µs pulse lengths delivered in trains with an 'on' energised time per train of 0.1 µs to 1000 µs repeated up to 1000 times at a frequency of 1 kHz to 1000 KHz.

Injecting a foam directly into the environment surrounding the cells rather than a liquid-only substance with the same active agent results in a less conductive environment, enabling more efficient cell permeabilization aiding in the efficacy of electroporation-based treatments.

The efficacy of cell permeabilization (pores being created on the cell membrane) created by short bipolar electrical pulses (<50 µs) is impacted by the tissue conductivity. Higher conductivity of the liquid solution surrounding the cells will result in higher currents which is deleterious to the treatment resulting in poorer cell permeabilization and pain sensation in the patient.

Conductivity increases around the cell are caused in part by the volume of fluid in the area and the local injection of an electroporation solution, which may include a treatment molecule of choice (Calcium, Potassium, Bleomycin, Cisplatin etc) and a large concentration of ions.

Utilising a foaming agent to deliver the therapeutic agent reduces the effect of a high conductivity on the efficacy of electroporation pulses to permeabilise cells.

A foam being made largely of gas or air is less conductive than the corresponding liquid solution and consequently results in lower currents, higher cell permeabilization and less pain sensation for the patient.

Use of a foam injected into the environment to be electroporated will beneficially facilitate the treatment and the degree of cell permeabilization by not increasing the conductivity to the degree that a comparable liquid solution would. The following table sets out some preferred parameter ranges where a foam is injected, but these ranges advantageously apply to liquid injection.

| Treatment | Pulse Voltage V/cm | Pulse duration | Frequency Hz | Number of Pulses | Charge Delivered | Pulse Type |
|---|---|---|---|---|---|---|
| Electrochemotherapy (ECT) | 500-1500 | 50-100 μsec | 1-5000 | 4-8 | N/A | Monopolar or Bipolar Square wave |
| Irreversible electroporation (IRE) | 1500-3000 | 70-100 μsec | 0.5-10 | 90-200 | N/A | Monopolar Square wave |
| High Freq Irreversible electroporation (HFIRE) | 2500-5000 | 1-5 μs | 100-500 KHz | >100 | N/A | Monopolar or Bipolar Square wave |
| Electroporation and Electrolysis (E2) | 100-3000 | μsec-milliseconds | N/A | N/A | >100 μF | Exponentially decaying wave |
| DNA/RNA delivery | 1-1000 | μsec-milliseconds | N/A | N/A | N/A | Monopolar Square wave |

A foam may also be utilised to facilitate dispersion of a local anaesthetic into the tissue to be treated. The local anaesthetic may be lignocaine 5-20 mg/ml with or without adrenaline. Mepivacaine 10 to 30 mg/ml is another example of a local anaesthetic that could be used. The foam and local anaesthetic could be administrated in combination with a molecule of choice e.g. calcium or potassium ions, bleomycin, DNA; or it could be provided alone.

Apparatus for Injection of Substance (Liquid Only or Foam)

Figure 19:
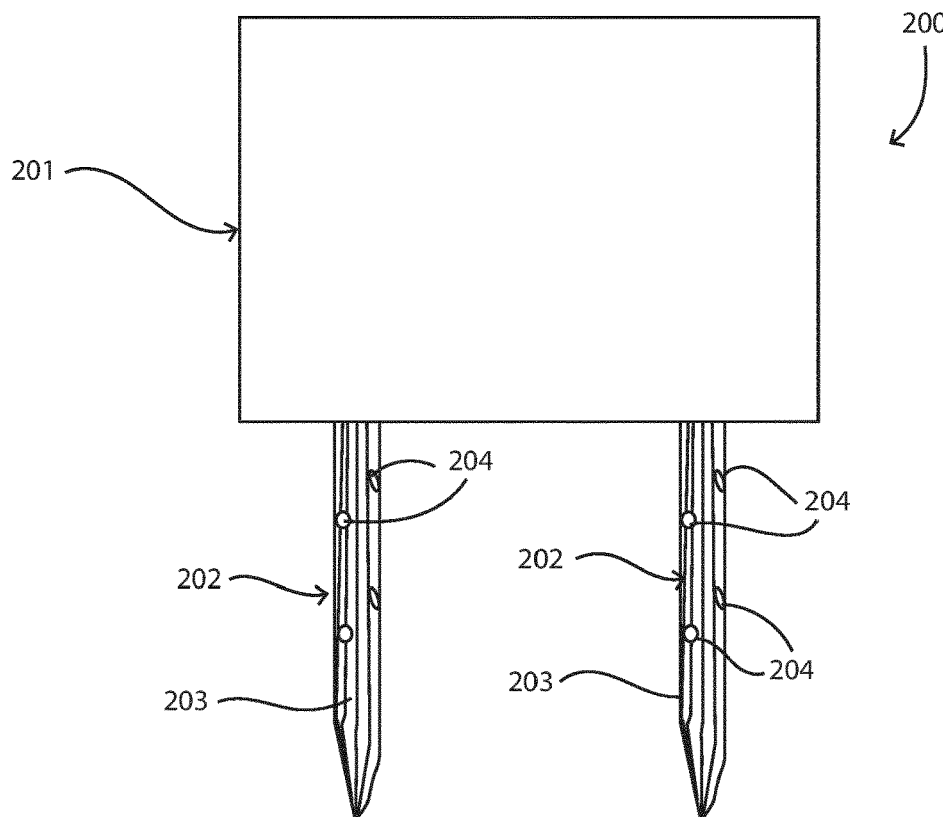
FIG. 19 is a diagram showing a foam injection head of an electroporation apparatus.

Referring to FIG. 19 an injection apparatus is used to deliver the substance to the target tissue via a needle electrode that can also facilitate homogenous distribution of an injected substance via 'pores' or openings along its conductive length. In one example the apparatus, 200, comprises a reservoir 201 and an array of needles 202 with walls 203 and pores 204. The reservoir 201 comprises a pump of any desired type, such as a peristaltic pump or a syringe. The needle gauge size is preferably in the range of 14 GA to 30 GA (0.3 mm to 2.1 mm outer diameter; 0.15 mm to 1.8 mm inner diameter). More generally, it is preferred that the needles have a maximum internal width dimension in the range of 0.1 mm to 1.8 mm and a maximum external width dimension in the range of 0.25 mm to 2.5 mm 90, and preferably the openings have a maximum width dimension in the range of 0.05 mm to 1.5 mm, and preferably the separation of a needle to the closest needle is in the range of 2 mm to 3 cm.

In other examples the openings may be in the form of slots or holes of any desired shape to achieve the desired flow and distribution of injected substance. The needles may have an insulating sleeve to cover openings and/or to insulate electrically where voltage is not to be applied to the patient tissue. A sleeve, either insulated or not, may be removed after delivery of the substance and prior to pulsing. The pattern of the openings is preferably spiral (staggered) as shown in FIG. 19. The number of openings may be distributed unevenly, being weighted more towards the needle side facing the other needle(s)/electrode(s) to help ensure that most of the volume is distributed in the space between the electrodes. Depth indicators may be used to communicate the depth of the openings with respect to the tissue depth.

The probe head 200 may be used with a pulse generator as described above, or with a known third-party electroporation generator.

The needles may all be connected to the same pump or reservoir, or may have independent pumps or valving arrangements to allow different substances be delivered through different needles. One or more needle may have its own solid trocar tip.

The injected substance may be a foam, but it could alternatively be a liquid-only substance such as a non-conductive substance, for example deionised water.

Figure 20:
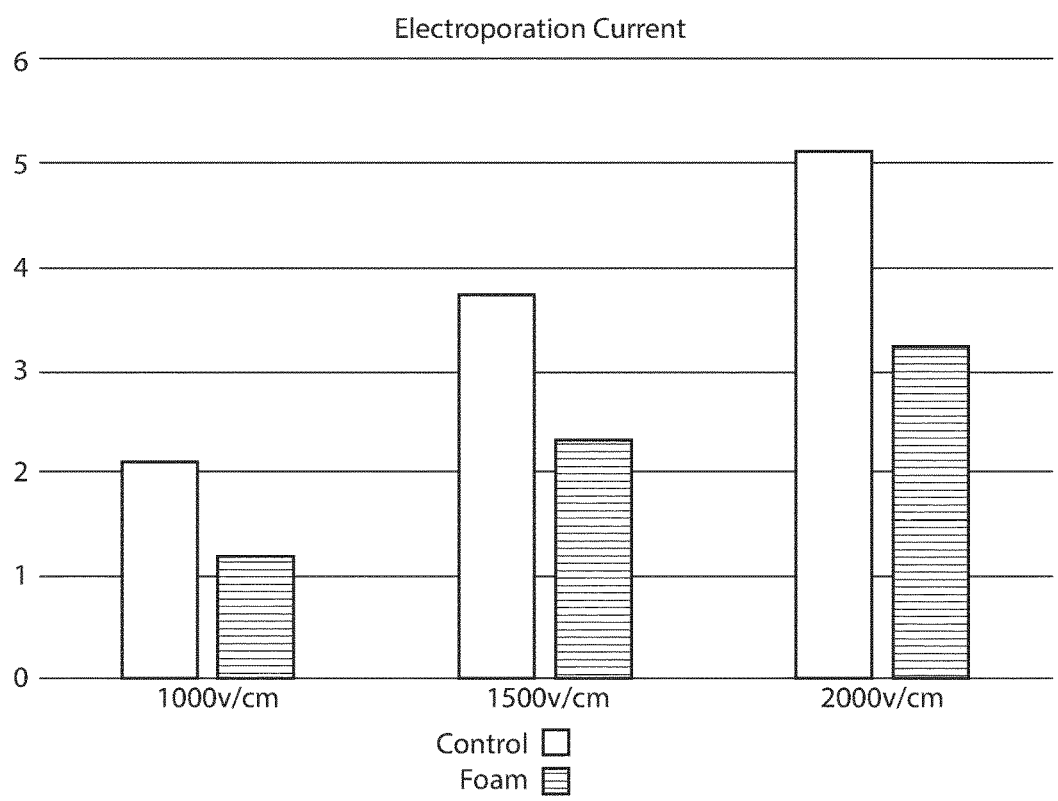
FIG. 20 is a plot showing reductions in electroporation currents arising from use of foam for various voltage drive levels.

Test data demonstrates that in a viable test tissue (animal liver) we evaluated the current generated during delivery of electroporation pulses with increasing voltage. The total energised 'on time' of the pulses was 6 ms. A reduction in the current generated per pulse delivered was approximately 40% when foam was injected into the tissue just prior to pulsing. FIG. 20 shows that in tests there is a major reduction in electroporation current for a given pulse voltage amplitude. In this plot the current units are Amps.

By using the probe of FIG. 19, the electrodes deliver the electrical pulses and also deliver the substance (liquid-only or foam) to tissue via the pores 204. This enables more homogenous delivery of the substance in the environment around the electrode. Also, it allows application of a co-ordinated substance delivery and pulsing method which may be controlled in an optimum manner by an electronic controller instructing the pulse generator and pumps and/or valves for substance delivery to needles. For example, in one programmed method there is injection to provide a desired level of conductivity, then pulsing, and then injection for access to cells which have been porated. The first substance may be a foam with a relatively high level of gas bubbles, and the post-pulsing solution may contain a therapeutic agent such as calcium, potassium, bleomycin or cisplatin or DNA or RNA.

The pores 204 deliver a foam or other substance such as a non-conductive solution e.g. deionized water directly into the tissue just prior to the electroporation pulse delivery and in doing so will reduce the current that would be generated otherwise. A higher current generated during a procedure will negatively impact on the efficacy of the electroporation pulses to porate the tissue. Generation of high currents also presents technical and safety challenges such as current 'arcing', tissue burning and pulse termination pre-procedure completion to protect the patient and the generator.

The needle electrodes 202 with pores 204 may be used to deliver a non-conductive solution just prior to delivery of the electrical pulses; additionally, the same electrodes may be used to administrate a therapeutic solution immediately once the electrical pulses have been delivered. In practice for example the needle electrode(s) are positioned in the target tissue and, in part based on impedance feedback, will inject a foam (or other solution) directly into the target tissue via the pores in the needle electrode(s). This is followed immediately by the delivery of the electrical pulses via the same needle electrode and there may be a post electroporation injection of a therapeutic substance directly via the needle electrode, for example a calcium or chemotherapeutic solution.

This optimizes the effect of the electroporation pulses while also enabling direct delivery of a therapeutic substance into the target tissue.

In the example of FIG. 19 there are two electrodes, positive and negative. In other examples there may be a bipolar single electrode where the negative and positive polarity are delivered on the same electrode. Alternatively, there may be more than 2 electrodes in an array such as described above with reference to FIG. 8.

Advantages

In general, it will be appreciated that the invention achieves very effective electroporation with minimal risk of patient discomfort. The following summarises some of the benefits.

There is improved DNA uptake, especially with an initial high frequency high voltage pulse (100 kHz to 500 kHz; 800V/cm to 1600V/cm bipolar) followed by low frequency and low voltage pulse as described above. It is especially advantageous that it is painless for the patient due to the high frequency nature of the high voltage pulses. The apparatus provides high frequency pulses with the aim of cell membrane and internal organelle permeabilization, causing ablation alone or in combination with a locally injected agent/molecule. We have described uptake of Calcium with a low concentration of injected Calcium as a liquid or foam, in a range of 2 to 150 mMol/L, preferably towards the lower end of this range. Also, high frequency pulses generate a reduced current by utilising a foam in the environment to be treated.

It will be appreciated that the apparatus achieves safe delivery of high voltage, ultra-short pulses (0.1 μs to 5.0 μs range) to human or animal subjects, whilst negating inefficiencies inherent to switch-mode transformer design.

The apparatus also achieves delivery of ultrashort pulses (μsec's) into a hyperosmotic solution enabling more efficient cell electroporation.

Furthermore, the apparatus enables combination of ultra-short pulses (μsec's) with sharp turn-on and turn-off times to maximise synergy with a consequent capacitance discharge in the range of 10-500 μF to induce localised cell death. It is particularly beneficial that the plateau is stable for significant but short duration of 1 μs to 3 μs, thereby achieving very effective treatment in a short energized on time.

Also, the apparatus' and methods achieve accurate coverage of tissue with sufficiently large electric field, avoiding the problem of uneven electric field distribution in tumour tissue due to its heterogeneity.

By use of an appropriate substance injected into the tissue, such as de-ionised liquid and/or a foam, lower conductivity is achieved. The lower the conductivity, the stronger the electric field as the distribution of the electric field in tissue is determined by the flow of electric current through the tissue, and hence the above methods and apparatus help create a more homogeneous electric field, leading to more consistent results.

The invention is not limited to the embodiments described but may be varied in construction and detail.

The invention claimed is:

1. An electroporation apparatus comprising:
a plurality of electroporation probe terminals;
a transformer for providing stepped-up voltage,
a switching circuit with switches for linking high voltage and low voltage or ground levels to the probe terminals; and
a controller configured to control said switches according to a control scheme to deliver pulses to the probe terminals, and in which said pulses are delivered to groups of at least two probe electrode terminals for probe electrodes which are spaced apart, and
wherein the controller is configured to apply a ramp-up ($t_r$) duration of less than 0.5 μs to a plateau amplitude in the range of 100V to 3000V for a duration in the range of 1 μs to 5 μs, and a ramp-down ($t_f$) duration from said voltage of less than 0.5 μs for each probe electrode terminal.

2. The electroporation apparatus as claimed in claim 1, wherein the pulses are bipolar for a pair of electrodes, and wherein each terminal of a pair is sequentially driven at a voltage amplitude and grounded out of phase with its corresponding probe terminal.

3. The electroporation apparatus as claimed in claim 1, wherein the amplitude is in the range of 700V to 1600V and the pulse plateau duration is in the range of 1 μs to 3 μs, and preferably the energized on-time during which pulses are delivered is in the range of 100 μs to 300 μs.

4. The electroporation apparatus as claimed in claim 1, wherein the pulses are bipolar for a pair of electrodes, and wherein each terminal of a pair is sequentially driven at a voltage amplitude and grounded out of phase with its corresponding probe terminal, and wherein the bipolar frequency is in the range of 100 kHz to 500 kHz.

5. The electroporation apparatus as claimed in claim 1, wherein the controller is configured to apply, after electroporation operation, a plateau of near to zero duration and to allow a ramp-down decay in a pulse, and preferably the rate of decay is set by permanent or adjustable values of resistors across charged capacitors.

6. The electroporation apparatus as claimed in claim 1, wherein the controller is configured with mapping data defining relative physical positions of probe terminals to be connected to the terminals, and to direct pulses for applying voltages across space bounded by the probe electrodes.

7. The electroporation apparatus as claimed in claim 1, wherein the controller is configured with mapping data defining relative physical positions of probe terminals to be connected to the terminals, and to direct pulses for applying voltages across space bounded by the probe electrodes; and wherein the controller is configured to simultaneously drive a first group of terminals with the same potential and an opposed second group with a different potential, for application of a charge across and between a plane defined by said first and second mapped probe locations, and wherein the first group are driven with a high potential and the second group are grounded.

8. The electroporation apparatus as claimed in claim 1, wherein the controller (2, 5) is configured to immediately reverse the direction across the plane, with the first group being applied with the potential previously applied to the second group and vice versa, in which the first and second groups are re-defined so that charge is applied in one direction across the space and then immediately reversed.

9. The electroporation apparatus as claimed in claim 1, wherein the controller is configured with mapping data defining relative physical positions of probe terminals to be connected to the terminals, and to direct pulses for applying voltages across space bounded by the probe electrodes; and wherein the controller is configured to, after reversing the direction across the plane, then drive third and fourth groups which also define said plane but the direction between the third and fourth groups is different from that between the first and second groups.

10. The electroporation apparatus as claimed in claim 1, wherein the controller is configured with mapping data defining relative physical positions of probe terminals to be connected to the terminals, and to direct pulses for applying voltages across space bounded by the probe electrodes; and wherein the controller is configured to, after reversing the direction across the plane, then drive third and fourth groups which also define said plane but the direction between the third and fourth groups is different from that between the first and second groups; and wherein said directions are approximately orthogonal; and wherein the mapping data is for a plane defined by at least one quadrangle bounded by four probes.

11. The electroporation apparatus as claimed in claim 1, wherein the switching circuit comprises a switch dedicated to each voltage level for each terminal.

12. The apparatus as claimed in claim 1, wherein the switching circuit comprises a switch dedicated to each voltage level for each terminal; and wherein the switching circuit comprises a switch dedicated to a high voltage level applied as a pulse to a terminal, and a switch dedicated to grounding the terminal; and wherein the switching circuit comprises a driver circuit dedicated to each switch.

13. The electroporation apparatus as claimed in claim 1, wherein each driver circuit is individually addressable by the controller; and wherein the switching circuit comprises a switch dedicated to each voltage level for each terminal; and wherein the switching circuit comprises a switch dedicated to a high voltage level applied as a pulse to a terminal, and a switch dedicated to grounding the terminal; and wherein the switching circuit comprises a driver circuit dedicated to each switch.

14. The electroporation apparatus as claimed in claim 1, wherein the switching circuit comprises a switch dedicated to each voltage level for each terminal; and wherein the switching circuit comprises a switch dedicated to a high voltage level applied as a pulse to a terminal, and a switch dedicated to grounding the terminal; and wherein the switching circuit comprises a driver circuit dedicated to each switch; and wherein each driver circuit comprises an independent floating power supply.

15. The electroporation apparatus as claimed in claim 1, wherein the switches include FETs, and/or GaN Transistors, and/or SiC Transistors and/or IGBTs.

16. The electroporation apparatus as claimed in claim 1, wherein the controller is configured to perform a probe interrogation initially, to determine from a probe memory a desired driving profile, and optionally the probe interrogation is performed by the controller to set the optimal parameters for the probe.

17. The electroporation apparatus of claim 1, wherein the controller is configured to measure the impedance in a biological load by applying an AC signal to probe electrodes over a frequency spectrum, and optionally the frequency spectrum is in the range of 1 kHz to 100 kHz.

18. The electroporation apparatus as claimed in claim 1, wherein the controller is configured to measure the impedance in a biological load by applying an AC signal to probe electrodes over a frequency spectrum, and optionally the frequency spectrum is in the range of 1 kHz to 100 kHz; and wherein the impedance measurement is performed before electroporation driving, and the controller is configured to automatically adjust drive parameters according to said measured impedance, preferably to achieve a current flow across a pair of electrodes of less than 500 mA.

19. The electroporation apparatus of claim 1 and a plurality of probe electrodes connected to said probe terminals.

20. The electroporation apparatus as claimed in claim 1, and a plurality of probe electrodes connected to said probe terminals; and wherein the probe electrodes are in a probe head comprising at least one electrode needle which is hollow and has at least one opening for flow of a substance into tissue.

21. The electroporation apparatus as claimed in claim 1, and a plurality of probe electrodes connected to said probe terminals; and the probe electrodes are in a probe head comprising at least one electrode needle which is hollow and has at least one opening for flow of a substance into tissue wherein controller is configured to control flow of a substance to the one or more needles in a method also including driving the needles with pulses.

22. A method of operation of an electroporation apparatus comprising:
  a plurality of electroporation probe terminals;
  a transformer for providing stepped-up voltage,
  a switching circuit with switches for linking high voltage and low voltage or ground levels to the probe terminals; and
  a controller configured to control said switches according to a control scheme to deliver pulses to the probe terminals, and in which said pulses are delivered to groups of at least two probe electrode terminals for probe electrodes which are spaced apart, and
  a plurality of probe electrodes connected to said probe terminals; and the probe electrodes are in a probe head comprising at least one hollow electrode needle which is hollow and has at least one opening,
the method comprising:
  inserting said probe electrodes into a biological load,
  the controller applying bi-polar voltage pulses into the electrodes and the load for electroporation, in which the controller applies a ramp-up ($t_r$) duration of less than 0.5 µs to a plateau amplitude in the range of 100V to 3000V for a duration in the range of 1 µs to 5 µs, and a ramp-down ($t_f$) duration from said voltage of less than 0.5 µs for each probe electrode terminal, and
  causing flow of a substance into tissue via said needle and said opening, wherein the controller controls flow of said substance to the one or more hollow needles while driving said needle or needles with said pulses.

* * * * *